(12) United States Patent
Bonde et al.

(10) Patent No.: US 11,534,200 B2
(45) Date of Patent: Dec. 27, 2022

(54) CANNULA CONFIGURED TO DELIVER TEST STIMULATION

(71) Applicant: Medtronic, Inc., Minneapolis, MN (US)

(72) Inventors: Eric H. Bonde, Minnetonka, MN (US); Martin T. Gerber, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 582 days.

(21) Appl. No.: 16/544,105

(22) Filed: Aug. 19, 2019

(65) Prior Publication Data

US 2019/0366105 A1 Dec. 5, 2019

Related U.S. Application Data

(60) Continuation of application No. 15/200,275, filed on Jul. 1, 2016, now Pat. No. 10,413,736, which is a
(Continued)

(51) Int. Cl.
*A61N 1/05* (2006.01)
*A61B 17/34* (2006.01)
(Continued)

(52) U.S. Cl.
CPC .......... *A61B 17/3415* (2013.01); *A61B 90/39* (2016.02); *A61N 1/0551* (2013.01);
(Continued)

(58) Field of Classification Search
CPC . A61B 90/39; A61B 17/3415; A61B 17/3403; A61B 17/3468;
(Continued)

(56) References Cited

U.S. PATENT DOCUMENTS 2,717,600 A 9/1955 Jennie
4,136,703 A 1/1979 Wittkampf
(Continued)

FOREIGN PATENT DOCUMENTS

DE 202004017861 U1 2/2005
EP 0922466 A2 6/1999
(Continued)

OTHER PUBLICATIONS

"Destino Twist, Deflectable Steerable Guiding Sheath," Oscor, Aug. 2014, 2 pp.
(Continued)

*Primary Examiner* — Tammie K Marlen
(74) *Attorney, Agent, or Firm* — Shumaker & Sieffert, P.A.

(57) ABSTRACT

The disclosure is directed to an implant tool and cannula used to facilitate the implantation of a medical device into a patient. The implant tool includes a housing that is held by a user and a needle attached to the housing. The cannula may be positioned over the needle and delivered to a target tissue within the patient. The cannula includes an electrode at a distal portion to deliver test stimulation to confirm the location of the target site or placement of the implant tool relative to the target site before removing the needle of the implant tool. In this manner, the cannula may be repositioned within the patient until the position of the implant tool and cannula relative to the target site is verified with the test stimulation.

27 Claims, 19 Drawing Sheets

Related U.S. Application Data division of application No. 11/740,079, filed on Apr. 25, 2007, now Pat. No. 9,399,130.

(51) Int. Cl.
  *A61N 1/36* (2006.01)
  *A61B 90/00* (2016.01)
  *A61N 1/372* (2006.01)
  *A61B 17/00* (2006.01)

(52) U.S. Cl.
  CPC ......... *A61N 1/0558* (2013.01); *A61N 1/3605* (2013.01); *A61N 1/37241* (2013.01); *A61B 2017/00039* (2013.01); *A61B 2090/3937* (2016.02)

(58) Field of Classification Search
  CPC .. A61B 2090/3937; A61B 2017/00039; A61N 1/0551; A61N 1/0558; A61N 1/3605; A61N 1/37241; A61N 1/0573; A61N 1/0592
  See application file for complete search history.

(56) References Cited

U.S. PATENT DOCUMENTS

| | | | |
|---|---|---|---|
| 4,141,365 A | 2/1979 | Fischell et al. | |
| 4,512,351 A * | 4/1985 | Pohndorf | A61N 1/0551 607/117 |
| 4,630,611 A | 12/1986 | King | |
| 4,676,249 A | 6/1987 | Arenas et al. | |
| 4,808,157 A | 2/1989 | Coombs | |
| 4,815,478 A | 3/1989 | Buchbinder et al. | |
| 4,922,910 A | 5/1990 | Kanai et al. | |
| 4,940,062 A | 7/1990 | Hampton et al. | |
| 4,961,434 A | 10/1990 | Stypulkowski | |
| 4,966,583 A * | 10/1990 | Debbas | A61M 25/10 604/98.01 |
| 5,000,194 A | 3/1991 | van den Honert et al. | |
| 5,040,543 A | 8/1991 | Badera et al. | |
| 5,152,749 A | 10/1992 | Giesy et al. | |
| 5,170,787 A | 12/1992 | Lindegren | |
| 5,255,691 A | 10/1993 | Otten | |
| 5,327,906 A | 7/1994 | Fideler | |
| 5,391,199 A | 2/1995 | Ben-Haim | |
| 5,423,877 A | 6/1995 | Mackey | |
| 5,443,492 A | 8/1995 | Stokes et al. | |
| 5,522,874 A | 6/1996 | Gates | |
| 5,562,695 A | 10/1996 | Obenchain | |
| 5,630,836 A | 5/1997 | Prem et al. | |
| 5,649,970 A | 7/1997 | Loeb et al. | |
| 5,662,119 A | 9/1997 | Brennen et al. | |
| 5,662,694 A | 9/1997 | Lidman et al. | |
| 5,669,882 A | 9/1997 | Pyles | |
| 5,728,148 A | 3/1998 | Bostrom et al. | |
| 5,800,465 A | 9/1998 | Thompson et al. | |
| 5,824,031 A | 10/1998 | Cookston et al. | |
| 5,830,188 A | 11/1998 | Abouleish | |
| 5,843,148 A | 12/1998 | Gijsbers et al. | |
| 5,899,909 A | 5/1999 | Claren et al. | |
| 6,038,480 A | 3/2000 | Hrdlicka et al. | |
| 6,059,739 A | 5/2000 | Baumann | |
| 6,104,957 A | 8/2000 | Alo et al. | |
| 6,238,389 B1 | 5/2001 | Paddock et al. | |
| 6,241,724 B1 * | 6/2001 | Fleischman | A61B 18/1492 600/374 |
| 6,249,707 B1 | 6/2001 | Kohnen et al. | |
| 6,360,750 B1 | 3/2002 | Gerber et al. | |
| 6,473,653 B1 | 10/2002 | Schallhorn et al. | |
| 6,493,590 B1 | 12/2002 | Wessman et al. | |
| 6,510,347 B2 | 1/2003 | Borkan | |
| 6,553,264 B2 | 4/2003 | Redko et al. | |
| 6,569,160 B1 * | 5/2003 | Goldin | A61B 18/1492 606/49 |
| 6,587,733 B1 | 7/2003 | Cross, Jr. et al. | |
| 6,592,573 B2 | 7/2003 | Castaneda et al. | |
| 6,607,496 B1 | 8/2003 | Poor et al. | |
| 6,733,500 B2 | 5/2004 | Kelley et al. | |
| 6,757,970 B1 | 7/2004 | Kuzma et al. | |
| 6,805,675 B1 | 10/2004 | Gardeski et al. | |
| 6,836,687 B2 | 12/2004 | Kelley et al. | |
| 6,847,849 B2 | 1/2005 | Mamo et al. | |
| 6,971,393 B1 | 12/2005 | Mamo et al. | |
| 6,999,819 B2 | 2/2006 | Swoyer et al. | |
| 7,056,314 B1 | 6/2006 | Florio et al. | |
| 7,065,412 B2 | 6/2006 | Swoyer et al. | |
| 7,220,242 B2 | 5/2007 | Putter et al. | |
| 7,328,071 B1 | 2/2008 | Stehr et al. | |
| 7,544,197 B2 | 6/2009 | Kelsch et al. | |
| 7,640,059 B2 | 12/2009 | Forsberg et al. | |
| 7,668,601 B2 | 2/2010 | Hegland et al. | |
| 7,680,540 B2 | 3/2010 | Jensen et al. | |
| 7,763,034 B2 | 7/2010 | Siegel et al. | |
| 8,180,461 B2 | 5/2012 | Mamo et al. | |
| 9,399,130 B2 | 7/2016 | Bonde et al. | |
| 9,427,574 B2 | 8/2016 | Lee et al. | |
| 9,531,555 B2 | 12/2016 | Howard et al. | |
| 9,561,053 B2 | 2/2017 | Bonde et al. | |
| 9,802,038 B2 | 10/2017 | Lee et al. | |
| 9,855,423 B2 | 1/2018 | Jiang et al. | |
| 10,413,736 B2 | 9/2019 | Bonde et al. | |
| 2002/0147485 A1 | 10/2002 | Mamo et al. | |
| 2002/0183817 A1 | 12/2002 | Van Venrooij et al. | |
| 2003/0028147 A1 | 2/2003 | Aves et al. | |
| 2003/0045919 A1 | 3/2003 | Swoyer et al. | |
| 2003/0083724 A1 | 5/2003 | Jog et al. | |
| 2003/0171644 A1 | 9/2003 | Anderson et al. | |
| 2003/0176875 A1 | 9/2003 | Anderson et al. | |
| 2003/0212305 A1 | 11/2003 | Anderson et al. | |
| 2003/0236557 A1 | 12/2003 | Whitehurst et al. | |
| 2004/0015204 A1 | 1/2004 | Whitehurst et al. | |
| 2004/0015205 A1 | 1/2004 | Whitehurst et al. | |
| 2004/0059280 A1 | 3/2004 | Makower et al. | |
| 2004/0098074 A1 | 5/2004 | Erickson et al. | |
| 2004/0138527 A1 | 7/2004 | Bonner et al. | |
| 2004/0138675 A1 | 7/2004 | Crabtree | |
| 2004/0172090 A1 | 9/2004 | Janzig et al. | |
| 2004/0193228 A1 | 9/2004 | Gerber | |
| 2004/0210245 A1 | 10/2004 | Erickson et al. | |
| 2005/0033372 A1 | 2/2005 | Gerber | |
| 2005/0055063 A1 | 3/2005 | Loeb et al. | |
| 2005/0090728 A1 | 4/2005 | Mest | |
| 2005/0096667 A1 | 5/2005 | Smith et al. | |
| 2005/0234507 A1 | 10/2005 | Geske et al. | |
| 2005/0240238 A1 | 10/2005 | Mamo et al. | |
| 2005/0267555 A1 | 12/2005 | Marnfeldt et al. | |
| 2006/0058588 A1 | 3/2006 | Zdeblick | |
| 2006/0089633 A1 | 4/2006 | L. Bleich et al. | |
| 2006/0095079 A1 | 5/2006 | Gerber | |
| 2006/0129101 A1 | 6/2006 | McGuckin, Jr. | |
| 2006/0168805 A1 | 8/2006 | Hegland et al. | |
| 2006/0173262 A1 | 8/2006 | Hegland et al. | |
| 2007/0027515 A1 | 2/2007 | Gerber | |
| 2007/0173900 A1 | 7/2007 | Siegel et al. | |
| 2007/0203546 A1 | 8/2007 | Stone et al. | |
| 2007/0260295 A1 | 11/2007 | Chen et al. | |
| 2008/0200769 A1 | 8/2008 | Sharma et al. | |
| 2008/0269716 A1 | 10/2008 | Bonde et al. | |
| 2008/0269763 A1 | 10/2008 | Bonde et al. | |
| 2011/0106100 A1 | 5/2011 | Bischoff | |
| 2011/0257710 A1 | 10/2011 | Ackermann et al. | |
| 2013/0110201 A1 | 5/2013 | Bonde et al. | |
| 2013/0274843 A1 | 10/2013 | Barker et al. | |
| 2013/0317588 A1 | 11/2013 | Howard et al. | |

FOREIGN PATENT DOCUMENTS

| | | |
|---|---|---|
| EP | 1048270 A1 | 11/2000 |
| EP | 1048271 A2 | 11/2000 |
| EP | 1342454 A1 | 9/2003 |
| EP | 0832667 B1 | 2/2004 |
| FR | 2688407 A1 | 9/1993 |
| WO | 02068042 A1 | 9/2002 |

(56) References Cited

FOREIGN PATENT DOCUMENTS

| WO | 2003084398 A1 | 10/2003 |
|---|---|---|
| WO | 2005009531 A1 | 2/2005 |
| WO | 2005032650 A1 | 4/2005 |
| WO | 2005118057 A2 | 12/2005 |
| WO | 2006133445 A2 | 12/2006 |

OTHER PUBLICATIONS

Abrams et al., "The role of neuromodulation in the management of urinary urge incontinence," British Journal of Urology International, vol. 91, No. 4, Mar. 2003, pp. 355-359.

Extended Search Report from counterpart European Application No. 10002241.7, dated May 25, 2010, 7 pp.

International Preliminary Report on Patentability from International Application No. PCT/US2008/059355, dated Apr. 24, 2009, 11 pp.

International Search Report and Written Opinion of International Application No. PCT/US2008/059355, dated Aug. 6, 2008, 16 pp.

Ishigooka et al., "A new technique for sacral nerve stimulation: a percutaneous method for urinary incontinence caused by spinal cord injury," British journal of Urology, vol. 81, No. 2, Feb. 1998, pp. 315-318.

Prosecution History from U.S. Appl. No. 11/740,049, dated Dec. 18, 2009 through Oct. 26, 2016, 151 pp.

Prosecution History from U.S. Pat. No. 9,399,130, dated Dec. 10, 2009 through Jun. 15, 2016, 211 pp.

Reply to Written Opinion dated Aug. 6, 2008, from International Application No. PCT/US2008/059355, filed Feb. 25, 2009, 13 pp.

Spinelli et al., "New Percutaneous Technique of Sacral Nerve Stimulation Has High Initial Success Rate: Preliminary Results," European Urology, vol. 43, No. 1, Jan. 2003, pp. 70-74.

Zhang et al., "The Permeability Characteristics of Silicone Rubber," Society for the Advancement of Material and Process Engineering, Nov. 6-9, 2006, 10 pp.

Prosecution History from U.S. Patent No. U.S. Appl. No. 15/200,275, dated Sep. 19, 2016 through May 6, 2019, 102 pp.

Elterman, "The novel Axonics® rechargeable sacral neuromodulation system: Procedural and technical impressions from an initial North American experience," Neurourology and Urodynamics, Feb. 2018, 8 pp.

Axonics System for Sacral Neuromodulation Overview, printed from https://www.axonics.com/hcp/axonics-system/system-overview on Feb. 3, 2020, 5 pp.

\* cited by examiner

CANNULA CONFIGURED TO DELIVER TEST STIMULATION

This application is a continuation of U.S. patent application Ser. No. 15/200,275, which was filed on Jul. 1, 2016, assigned U.S. Pat. No. 10,413,736, and is entitled, "CANNULA CONFIGURED TO DELIVER TEST STIMULATION," which is a divisional of U.S. patent application Ser. No. 11/740,079, which was filed on Apr. 25, 2007, and assigned U.S. Pat. No. 9,399,130, and is entitled, "CANNULA CONFIGURED TO DELIVER TEST STIMULATION." The entire content of U.S. patent application Ser. No. 15/200,275 and U.S. patent application Ser. No. 11/740,079 is incorporated herein by reference.

TECHNICAL FIELD

The invention relates to medical devices and, more particularly, devices for implanting other medical devices.

BACKGROUND

Electrical stimulation systems may be used to deliver electrical stimulation therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, or obesity. The electrical stimulation system may also be used for muscle stimulation, such as for function electrical stimulation of muscles. An electrical stimulation system typically includes one or more implantable medical leads coupled to an external or implantable electrical stimulator.

The implantable medical lead may be percutaneously or surgically implanted in a patient on a temporary or permanent basis such that at least one stimulation electrode is positioned proximate to a target stimulation site. The target stimulation site may be, for example, a nerve or other tissue site, such as a spinal cord, pelvic nerve, pudendal nerve, sacral nerve, peripheral nerve, stomach, bladder, or within a brain or other organ of a patient, or within a muscle or muscle group of a patient. The one or more electrodes located proximate to the target stimulation site may deliver electrical stimulation therapy to the target stimulation site in the form of electrical signals.

SUMMARY

In general, the disclosure relates to an implant tool and a cannula that may be used to facilitate the implantation of a medical device into a patient. The implant tool includes a housing that is held by a user and a needle attached to the housing. The needle is configured so that the cannula may be positioned over the needle and delivered to the target tissue site by the needle. Once the needle is in place relative to a target site within the patient, the needle is removed and a medical device may be implanted through the lumen of the cannula that remains within the patient. In one embodiment, a distal end of the needle is positioned proximate to the target site. The cannula includes an electrode at the distal end of the cannula to deliver test stimulation to a target site before removing the needle of the implant tool. In this manner, the cannula may be repositioned within the patient until the location of the implant tool and cannula relative to the target site is verified with the test stimulation. The cannula also includes an electrical contact at the proximal end of the cannula that couples to a source of electrical stimulation. For example, in one embodiment, the electrical contact at the proximal end of the cannula couples to an electrical contact of the implant tool and a conductive element electrically couples the electrode and the electrical contact.

In one embodiment, the disclosure is directed toward a cannula that includes an elongated housing defining a lumen configured to allow passage of a medical device. The cannula also includes an electrode positioned on a distal portion of the elongated housing, an electrical contact positioned on a proximal portion of the elongated housing, and a conductive element that resides within the elongated housing and electrically couples the electrode to the electrical contact.

In another embodiment, the disclosure is directed toward a system that includes a cannula and an implant tool. The cannula includes an elongated housing defining a lumen configured to allow passage of a medical device, an electrode positioned on a distal portion of the elongated housing, a first electrical contact positioned on a proximal portion of the elongated housing, and a conductive element that resides within the elongated housing and electrically couples the electrode to the electrical contact. The implant tool includes a needle coupled to a housing and configured to be inserted into tissue of a patient and to fit within an inner lumen of the cannula and a second electrical contact configured to electrically couple to the first electrical contact.

In another embodiment, the disclosure is directed toward a method that includes introducing a cannula and needle assembly into a patient, wherein the needle is at least partially disposed within a lumen of the cannula, and wherein the lumen is configured to allow passage of a medical device. The method also includes advancing the cannula to a target site within the patient and delivering test stimulation to the patient via an electrode positioned at a distal portion of the cannula.

The disclosure may provide one or more advantages. For example, the cannula includes an electrode at the distal end of the cannula to deliver test stimulation to the patient before removing the needle of the implant tool. In this manner, the user may use the needle to reposition the cannula and again attempt to verify the target site with the test stimulation. Utilizing test stimulation during implantation of a medical device may reduce the time, expense, and failed treatment associated with inaccurate implantation of medical devices, such as leads, catheters, and microstimulators. In addition, the cannula may have one or more partial-ring or segmented electrodes around the perimeter of the cannula that aid the user in identifying a direction of a target tissue site relative to the cannula. Identifying a direction of a target tissue site within the patient may be useful, for example, to discern a direction in which electrical stimulation may be delivered to provide efficacious therapy.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
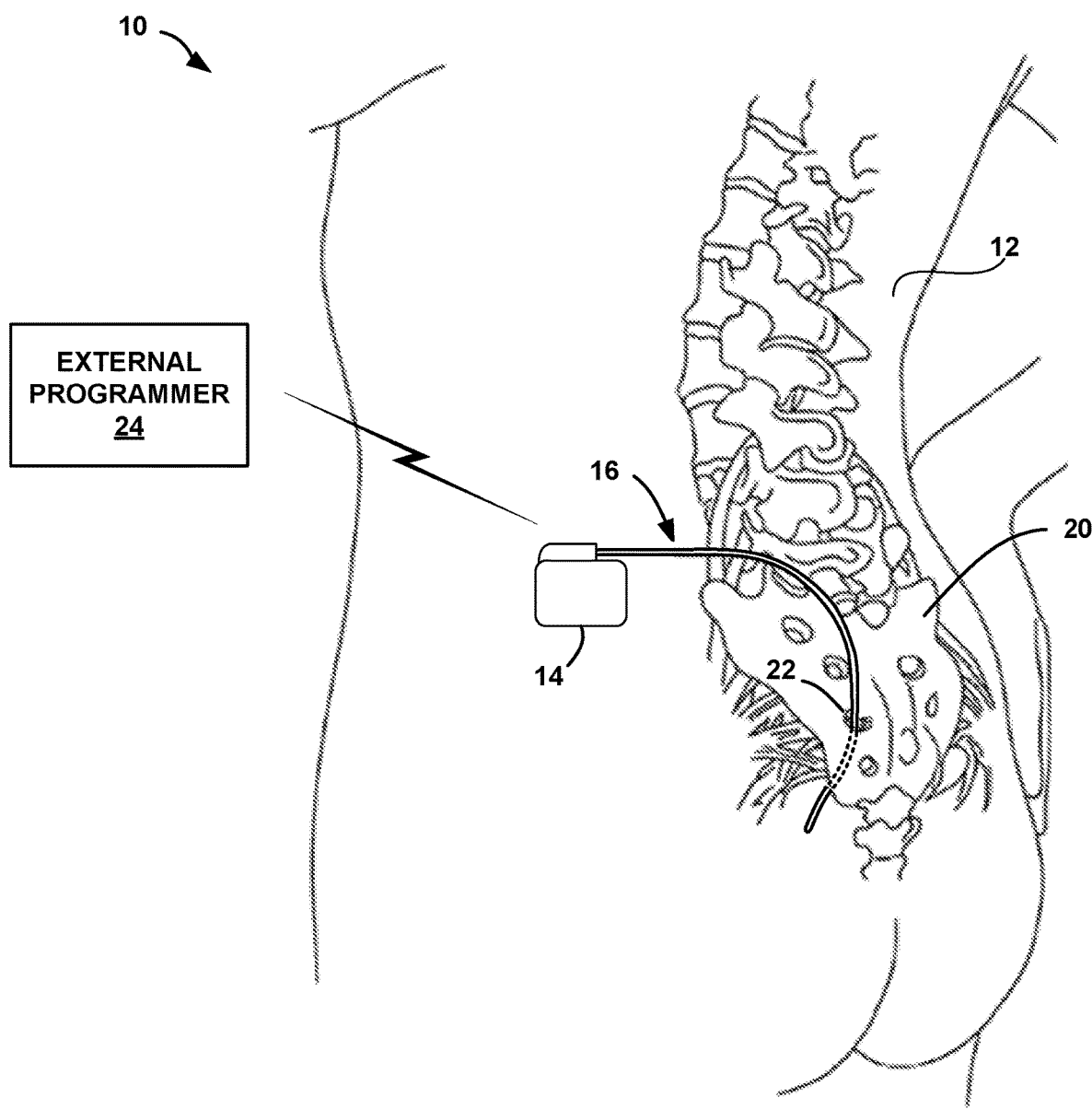
FIG. 1 is a perspective view of an example stimulation therapy system implanted in a patient to treat a tissue site in the pelvic floor of the patient.

Medical devices, such as medical leads or microstimulators, are implanted within a patient at a target site to treat a patient condition. Implant tools described herein include a needle that is introduced into the patient and a housing coupled to the needle to allow a user to manipulate the needle position when it is at least partially disposed within the patient. In one embodiment, the housing includes a cannula that is fitted over the needle before insertion of the needle into the patient so that the cannula may be introduced into a patient with the aid of the needle. Once the needle is correctly positioned at the target site, the user withdraws the needle from the cannula, leaving the cannula in place within the patient, such that the cannula defines a conduit that extends from outside of the patient to the target site. That is, the cannula defines an insertion path for a medical device that extends from an entry point accessible from outside of the patient to the target site. In this way, the cannula may also act as a "dilator" that dilates an insertion path defined by the needle in order to size the insertion path to receive a medical device. The user may then implant the desired medical device through the cannula and subsequently remove the cannula from the patient.

The implant tool also includes a release mechanism to facilitate the removal of the cannula from the needle. Static friction may hinder the withdrawal of the needle from the cannula. In such circumstances, the user must overcome static friction between the cannula and the needle to initiate the withdrawal of the needle from the cannula. The release mechanism is employed to overcome the static friction and aid in the removal of the needle without substantially changing the position of the distal end of the cannula with respect to the target site. In particular, release mechanism substantially inhibits the movement of the cannula away from target tissue site. Movement of the cannula in a deep direction toward the target tissue site (i.e., away from an entry point into the patient) may be inhibited by the resistance from tissue within the patient. The release mechanism allows the user to pull back on the housing of the implant tool and simultaneously push the cannula forward to ensure correct placement of the cannula. In this way, the release mechanism aids in counteracting friction forces between the cannula and needle that pull the cannula away from the target tissue site, where the forces are attributable to removal of the needle from the patient. In some embodiments, the release mechanism may be activated with one hand a user, leaving the user's other hand free for other purposes, such as to hold the cannula in place in order to further prevent movement of the cannula relative to a target tissue site.

In some examples, the implant tool and cannula may facilitate location of the tissue site for stimulation therapy. The cannula may have an electrode located at the distal end of the cannula to deliver test stimulation to identify the desired tissue site before implanting the medical device. In this manner, the user may correctly identify the tissue site for stimulation therapy before removing the implant tool from the patient. For example, based on patient feedback from the test stimulation, a clinician may adjust a position of the needle and cannula within the patient and, in some embodiments, deliver further test stimulation to confirm placement of the needle and cannula relative to the tissue site. The electrode of the cannula may be electrically coupled to an electrical contact at the proximal end of the cannula via a conductive element. In some embodiments, the conductive element is located within the cannula, such as embedded within the cannula or otherwise coupled to the cannula. The electrical contact may electrically couple to an electrical contact in the housing of the implant tool to transmit the test stimulation from the implant tool to the cannula. In addition, the test stimulation may be generated from a signal generator within the implant tool or an external signal generator connected to the implant tool. These and other examples are described in more detail below.

FIG. 1 is a prospective view of an example stimulation therapy system implanted in a patient to treat a tissue site in the pelvic floor of the patient. As shown in FIG. 1, system 10 includes stimulator 14, medical lead 16, and external programmer 24. Stimulator 14 and lead 16 are implanted within patient 12 and coupled such that stimulation 14 may deliver stimulation therapy to the patient via lead 16. Lead 16 is implanted through dorsal foramen 22 in sacrum 20 of patient 12 to access a target site within the patient. The target site may be a nerve or muscle within the pelvic floor of patient 12 to treat a variety of disorders. For example, system 10 may be provided to treat pelvic pain, urinary incontinence, fecal incontinence, constipation, sexual dysfunction, or other disorders. While stimulation therapy directed to pelvic floor tissue of patient 12 is generally described herein, stimulation therapy of any other tissue within the patient may also be provided. For example, system 10 may be provided for spinal cord stimulation therapy, peripheral nerve stimulation therapy, peripheral nerve field stimulation, deep brain stimulation, organ stimulation, muscle stimulation ((e.g., functional electrical stimulation (FES) of muscles) or any other stimulation therapy.

Stimulator 14 may provide stimulation therapy via electrical stimulation or drug delivery therapy. In the case of electrical stimulation, stimulator 14 may include a stimulation signal generator that generates an electrical signal (e.g., pulses or substantially continuous-time signals, such as sinusoidal signals) that is delivered to patient 12 via lead 16 that is configured to conduct the electrical signal. Lead 16 may have one or more electrodes positioned adjacent to a target tissue site that a user, e.g., a clinician or physician, desires to affect with the stimulation. Stimulator 14 generates the electrical signal according to one or more stimulation programs stored within a memory of the stimulator.

Alternatively, stimulator 14 may be configured to deliver a drug to patient 12. In the drug delivery example, stimulator 14 may store a volume of drug that is released to patient 12 in a controlled manner via lead 16. Stimulator 14 may have one or more programs that determine the amount and time for each bolus of drug for patient 12. Lead 16 may be a catheter with a lumen that allows the transfer of the drug from stimulator 14 to the target site of patient 12. In some examples, stimulator 14 may be configured to deliver multiple types of drugs or drugs in combination with electrical stimulation. In addition, multiple leads 16 may be implanted within patient 12 and connected to any stimulator 14.

Stimulator 14 may be programmed via communication with external programmer 24. External programmer 24 may be a clinician programmer or a patient programmer that is configured to communicate wirelessly with stimulator 14. External programmer 24 may allow a user, such as patient 12 or a clinician, to create stimulation programs, modify programs, view stimulation therapy history, interrogate stimulator 14 operability, and perform other tasks related to the therapy. External programmer 24 may include a user interface, processor, memory, telemetry circuit, and other components necessary for the function of the external programmer. In addition, external programmer may be embodied as a hand-held device, portable device, or a workstation, depending upon the configuration of system 10.

In the embodiment shown in FIG. 1, stimulator 14 is implanted within patient 12 at an implant site that is close to the target site in order to reduce the length of lead 16. In addition, the implant site for stimulator 14 may be selected to accommodate patient comfort and minimize the obtrusiveness of the implanted stimulator 14 to patient movement and daily activities. The location in which stimulator 14 resides may be, for example, a subcutaneous pocket created by a clinician and lead 16 may be tunneled through tissue from the target site to the pocket. In other examples, lead 16 may be coupled to a lead extension that is tunneled to stimulator 14 and coupled to the stimulator. In any case, stimulator 14 and lead 16 may be entirely implantable. Alternatively, stimulator 14 may be an external medical device and be coupled to lead 16 which percutaneously enters the patient. An external stimulator 14 may be useful for trial stimulation to evaluate the efficacy of chronic stimulation therapy.

As is described herein, an implant tool and cannula (not shown in FIG. 1) may be used to tunnel into patient 12 and access the target site for stimulation or other therapy deliver (e.g., drug delivery). Once the cannula is positioned within patient 12 by the implant tool, the cannula is used to pass lead 16 through tissue of the patient until the lead is positioned appropriately. In some cases, lead 16 may include a fixation structure or mechanism that secures at least the distal end of the lead in place adjacent to the target site. In any case, the implant tool may allow a clinician to implant lead 16 into patient 12 with a minimally invasive technique.

Figure 2A:
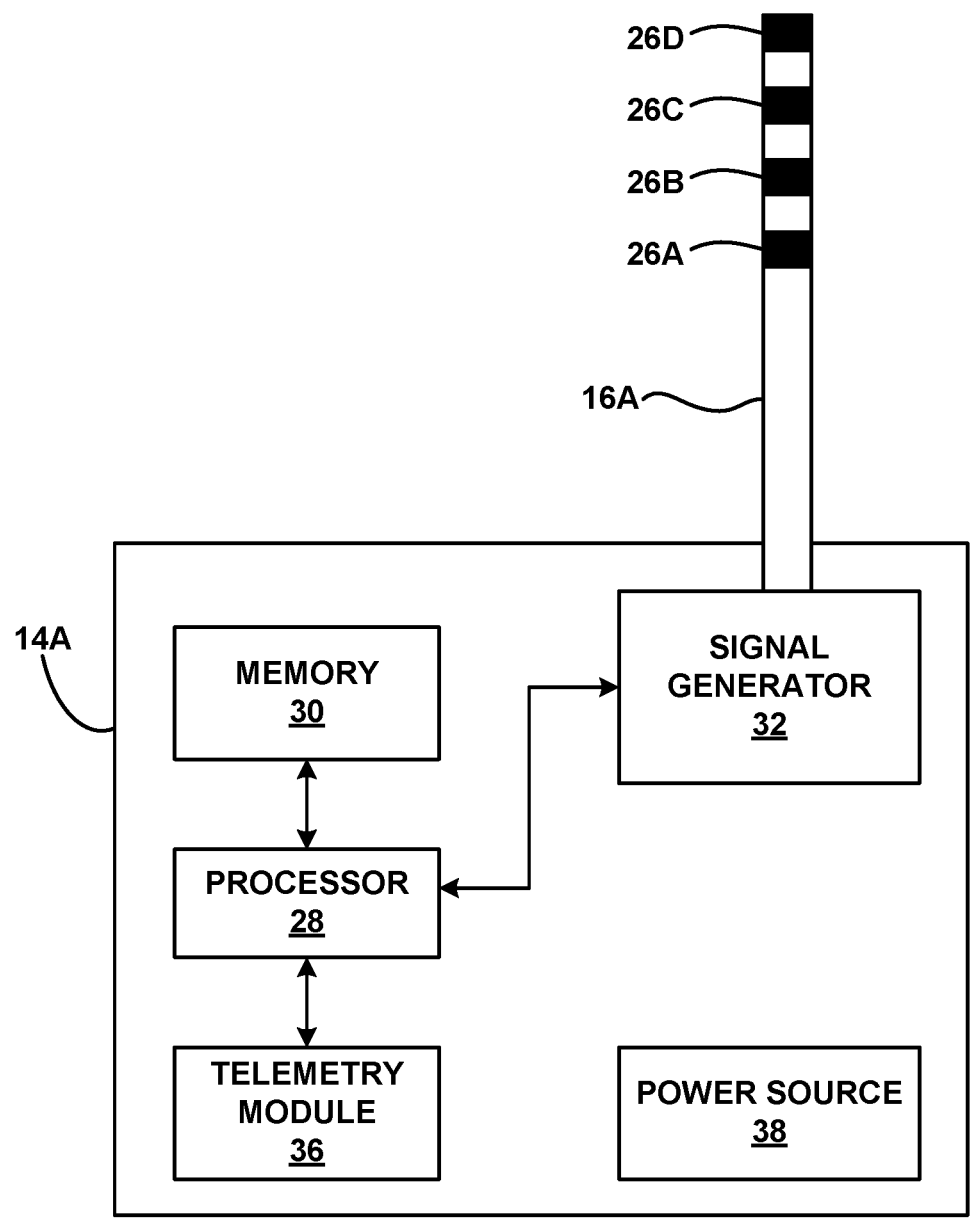
FIG. 2A is a block diagram of an example implantable stimulator for providing electrical stimulation therapy to a patient.

FIG. 2A is a block diagram of an example implantable stimulator 14A for providing electrical stimulation therapy to patient 12. Stimulator 14A includes signal generator 32, processor 28, memory 30, telemetry module 36, and power source 38. In some embodiments, stimulator 14A may also include a sensing circuit (not shown in FIG. 2A) for sensing a patient parameter, such as a physiological parameter (e.g., blood pressure, temperature or electrical activity) or an activity level of patient 12. Electrodes 26A, 26B, 26C, and 26D (collectively "electrodes 26") are disposed on lead 16A near a distal end of the lead. The configuration, type, and number of electrodes 26 illustrated in FIG. 2A are merely an example. In some embodiments, electrodes 26 may be ring electrodes. In other embodiments, electrodes 26 may be segmented or partial ring electrodes, each of which extends along an arc less than 360 degrees (e.g., 90-120 degrees) around the periphery, or circumference, of lead 16A.

In embodiments in which lead 16A is a paddle lead, electrodes 26 may extend along one side of lead 16A. Electrodes 26 extending around a portion of the circumference of lead 16A or along one side of a paddle lead may be useful for providing an electrical stimulation field in a particular direction/targeting a particular therapy delivery site or tissue site. For example, electrodes 26 may be disposed along lead 16A such that the electrodes face toward nerves within the tissue site of patient 12, or otherwise away from the undesired tissue. In addition, the use of segmented or partial ring electrodes 26 may also reduce the overall power delivered to electrodes 26 by stimulator 14A because of the efficient delivery of stimulation to the targeted nerve(s) or tissue by eliminating or minimizing the delivery of stimulation to unwanted or unnecessary regions within patient 12. Electrodes 26 of lead 16A may also extend along one side of lead 16A (if lead 16A includes a paddle-shaped portion) or may extend around a portion of lead 16A, as described with respect to electrodes 26 of lead 16A.

In embodiments in which electrodes 26 extend around a portion of the circumference of lead 16A or along one side of a paddle lead, lead 16A may include one or more orientation markers (not shown) proximate to the proximal end of lead 16A that indicates the relative location of electrodes 26. The orientation marker may be a printed marker on lead 16A, an indentation in lead 16A, a radiographic marker, or another type of marker that is visible or otherwise detectable (e.g., detectable by a radiographic device) by a clinician. The orientation marker may help a clinician properly orient lead 16A such that electrodes 26 face the desired direction (e.g., away from the scalp) when lead 16A is implanted within patient 12. For example, the orientation marker may also extend around the same portion of the circumference of lead 16A or along the side of the paddle lead as electrodes 26. In this way, the orientation marker faces the same direction as electrodes 26, thus indicating the orientation of electrodes 26 to the clinician. When the clinician implants lead 16A in the patient, the orientation marker may remain visible to the clinician.

Stimulator 14A delivers stimulation therapy to target tissue sites via electrodes 26 of lead 16A. Electrodes 26 are electrically coupled to a signal generator 32 of stimulator 14A via conductors within lead 16A. More specifically, the proximal end of lead 16A includes contacts (not shown) to electrically couple electrodes 26 directly to stimulator 14A or indirectly to stimulator 14A (e.g., via a lead extension). In one embodiment, an implantable signal generator or other stimulation circuitry within signal generator 32 delivers electrical signals (e.g., pulses or substantially continuous-time signals, such as sinusoidal signals) to target stimulation sites via at least some of electrodes 26 under the control of a processor 28. Signal generator 32 may also be coupled to power source 38. Power source 38 may take the form of a small, rechargeable or non-rechargeable battery, or an inductive power interface that transcutaneously receives inductively coupled energy. In the case of a rechargeable battery, power source 38 similarly may include an inductive power interface for transcutaneous transfer of recharge power.

The stimulation energy generated by signal generator 32 may be formulated as stimulation energy, e.g., for treatment of any of a variety of neurological disorders, or disorders influenced by patient neurological response. The signals may be delivered from signal generator 32 to electrodes 26 via a switch matrix and conductors carried by lead 16A and electrically coupled to respective electrodes 26.

Processor 28 may include a microprocessor, a controller, a digital signal processor (DSP), an application specific integrated circuit (ASIC), a field programmable gate array (FPGA), discrete logic circuitry, or the like. Processor 28 controls the implantable signal generator within signal generator 32 to deliver stimulation therapy according to selected stimulation parameters. Specifically, processor 28 controls signal generator 32 to deliver electrical signals with selected amplitudes, pulse widths (if applicable), and rates specified by the programs. In addition, processor 28 may also control signal generator 32 to deliver the stimulation signals via selected subsets of electrodes 26 with selected polarities. For example, electrodes 26 may be combined in various bipolar or multi-polar combinations to deliver stimulation energy to selected sites, such as nerve sites adjacent the spinal column, pelvic floor nerve sites, cranial nerve sites, peripheral nerve sites, or any other desires stimulation tissue sites.

Processor 28 may also control signal generator 32 to deliver each signal according to a different program, thereby interleaving programs or using multiple programs on each of a multiple of current sources to simultaneously treat different symptoms or provide a combined therapeutic effect. For example, in addition to treatment of one symptom such as urinary incontinence, stimulator 14A may be configured to deliver stimulation therapy to treat other symptoms such as pelvic pain. In such an embodiment, electrodes 26 of lead 16A may be positioned to deliver stimulation therapy for treating one symptom, and electrodes 26 of lead 16A may be positioned to deliver stimulation therapy for treatment of another symptom.

Memory 30 of stimulator 14A may include any volatile or non-volatile media, such as a RAM, ROM, NVRAM, EEPROM, flash memory, and the like. In some embodiments, memory 30 of stimulator 14A may store multiple sets of stimulation parameters that are available to be selected by patient 12 via external programmer 24 (FIG. 1) for delivery of stimulation therapy. For example, memory 30 may store stimulation parameters transmitted by external programmer 24 (FIG. 1). Memory 30 also stores program instructions that, when executed by processor 28, cause stimulator 14A to deliver stimulation therapy. Accordingly, computer-readable media storing instructions may be provided to cause processor 28 to provide functionality as described herein.

In particular, processor 28 controls telemetry module 36 to exchange information with external programmer 24, such as clinician programmer and/or a patient programmer, by wireless telemetry. In addition, in some embodiments, telemetry module 36 supports wireless communication with one or more wireless sensors that sense physiological signals and transmit the signals to stimulator 14A.

Figure 2B:
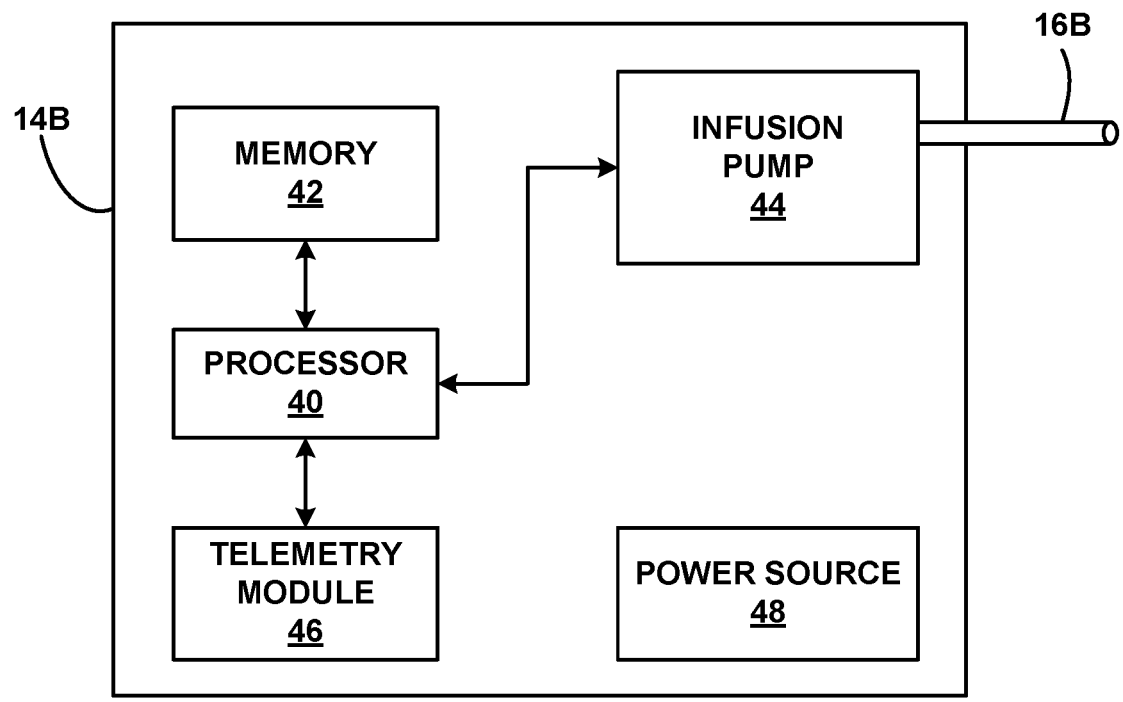
FIG. 2B is a block diagram of an example implantable fluid delivery device for providing drug delivery therapy to a patient.

FIG. 2B is a block diagram of an example implantable stimulator 14B for proving drug delivery therapy to patient 12. Stimulator 14B includes infusion pump 44, processor 40, memory 42, telemetry module 46, and power source 48. In some embodiments, stimulator 14B may also include a sensing circuit (not shown in FIG. 2B). Catheter 16B, e.g., a type of medical lead, is a drug delivery catheter coupled to infusion pump 44 to transmit drugs from stimulator 14B to the target site of patient 12.

Stimulator 14B delivers drug delivery therapy to one or more target tissue sites within patient 16 via catheter 16B. The distal end of catheter 16B may include one or more holes sized for effective transmission of the drug to the tissue. In some examples, catheter 16B may include a semi-porous region at the distal end of the catheter. In other examples, the drug may be delivered out of a very small opening at the distal end of catheter 16B to focus the drug at one small tissue site. In any event, infusion pump 44 includes circuitry and necessary mechanical components of a pump to release a bolus or rate of flow according to processor 40. Infusion pump 44 may also be coupled to power source 48. Power source 48 may take the form of a small, rechargeable or non-rechargeable battery, or an inductive power interface that transcutaneously receives inductively coupled energy. In the case of a rechargeable battery, power source 48 similarly may include an inductive power interface for transcutaneous transfer of recharge power.

Processor 40 may include a microprocessor, a controller, a DSP, an ASIC, an FPGA, discrete logic circuitry, or the like. Processor 40 controls infusion pump 44 to deliver drug therapy according to selected therapy parameters. Specifically, processor 40 controls infusion pump 44 to deliver the drug with selected rates, bolus sizes, intervals, and other parameters that may be used to define the delivery of drugs with infusion pump 44

Memory 42 of stimulator 14B may include any volatile or non-volatile media, such as a RAM, ROM, NVRAM, EEPROM, flash memory, and the like. In some embodiments, memory 42 of stimulator 14B may store multiple sets of therapy parameters that are available to be selected by patient 12 via external programmer 24 (FIG. 1) for delivery of stimulation therapy. For example, memory 42 may store stimulation parameters transmitted by external programmer 24 (FIG. 1). Memory 42 also stores program instructions that, when executed by processor 40, cause stimulator 14B to deliver stimulation drug therapy. Accordingly, computer-readable media storing instructions may be provided to cause processor 40 to provide functionality as described herein.

In particular, processor 40 controls telemetry module 46 to exchange information with external programmer 24, such as clinician programmer and/or a patient programmer, by wireless telemetry. In addition, in some embodiments, telemetry module 46 supports wireless communication with one or more wireless sensors that sense physiological signals and transmit the signals to stimulator 14B.

Figure 3A:
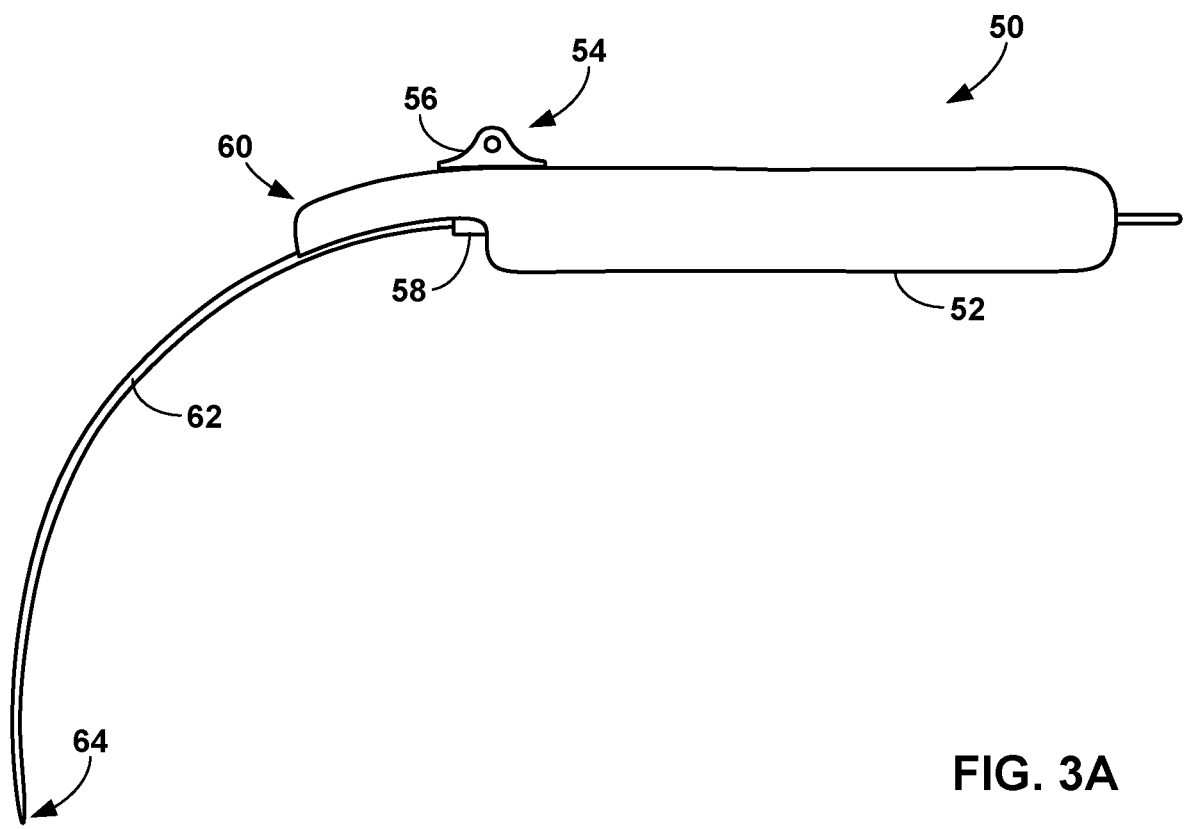
FIGS. 3A and 3B are side and top views, respectively, of an example implant tool having a release mechanism.
Figure 3B:
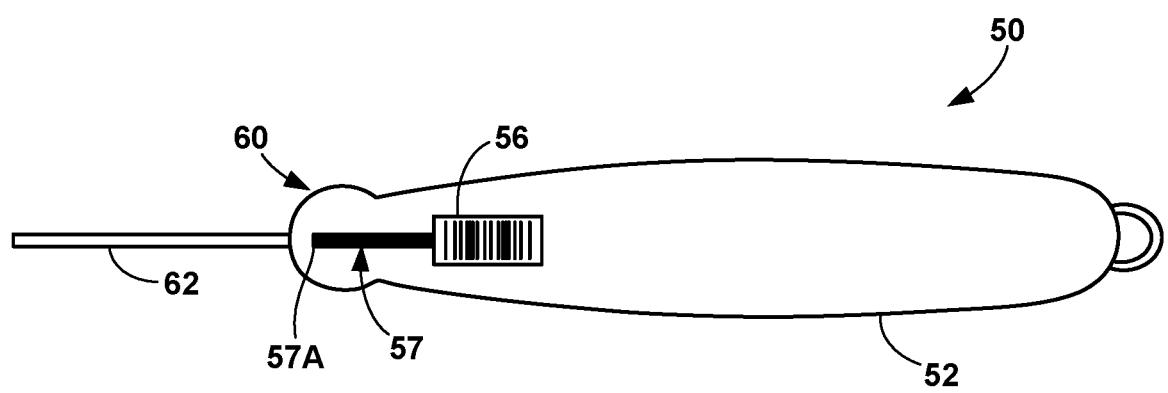

FIGS. 3A and 3B are side and top views, respectively, of an embodiment of an implant tool including a release mechanism. As shown in FIG. 3A, implant tool 50 includes housing 52, needle 62, and release mechanism 54. Needle 62 resides within a channel defined by housing 52 and has piercing tip 64 and a shape conducive for accessing the target site within patient 12 via an external tissue opening (e.g., an entry point through the skin of patient 12). Release mechanism 54 is coupled to housing 52 and includes grip 56 and guide 58 that allows a user to force a cannula (shown in FIGS. 4A-4B) off of needle 62.

Implant tool 50 may be configured to be held in a hand of a user. Housing 52 may have a shape that is simple for constructions and/or a shape that is ergonomically formed to rest within a human hand. Housing 52 may be constructed of substantial stiffness to resist flexing during use by the user. In addition, housing 52 defines a channel within the housing that secures needle 62 to the housing. The channel may have two or more segments which reside on two sides of housing 52 and, in some embodiments, engages with needle 62, to resist twisting torque applied to needle 62 from the user. Specifically, needle 62 may form a loop that matches a loop-shaped channel within housing 52 that secures the needle within the housing. Housing 52 also defines a slot that allows release mechanism to slide along the proximal portion of needle 62.

Housing 52 is also shaped to transmit force from the hand of the user to piercing tip 64 of needle 62. Housing 52 includes flange 60 positioned along one side of needle 62 that supports needle 62 when the user attempts to push piercing tip 64 through tissue of patient 12 and/or advance needle 62 through tissue. For example, when the user advances needle 62 through tissue of patient 12, needle 62 may contact and push against a substantially rigid flange 60, which helps prevent further movement of needle 62. In some embodiments, flange 60 may also define a semi-circular channel that follows along the length of needle 62 to distribute any force between flange 60 and needle 62 over a greater surface area of the needle. A space between the channel of flange 60 and needle 62 may allow the wall of a cannula to fit between the flange and the needle. In some examples, flange 60 may be shaped to surround a greater or lesser portion of needle 62. In other examples, flange 60 may completely surround needle 62 to support movements of the needle in any direction within patient 12 when introducing the needle into tissue of the patient.

Release mechanism 54 includes grip 56, guide 58, and a member (not shown) connecting the grip and the guide. Release mechanism 54 is configured to apply force against the end of a cannula substantially in a direction toward piercing tip 64 of needle 62 or otherwise away from housing 52. For example, the user may press a thumb, finger or another object against grip 56 to slide release mechanism 54 along needle 62. As the user withdraws housing 52 and needle 62 from an insertion path through tissue of the patient and from the cannula, the user may substantially simultaneously press a thumb, finger or another object against grip 56, which contacts the cannula via guide 58, thereby counteracting any forces (e.g., static friction forces) that may cause the cannula that is disposed at least partially around needle 62 from being unintentionally withdrawn from the insertion path through along with needle 62. In this manner, the user may withdraw needle 62 from the cannula while keeping the cannula substantially stationary relative to patient 12 and the target tissue site. While guide 58 is shown as a cylinder completely surrounding needle 62, the guide may only partially surround the needle in other embodiments.

Housing 52 and release mechanism 54 may be constructed of a variety of materials, such as a lightweight molded plastic, e.g., polystyrene. In other embodiments, other injection molded plastics may be used such as polyurethane, polypropylene, high molecular weight polyurethane, polycarbonate or nylon. Alternatively, construction materials may include aluminum, stainless steel, a metal alloy or a composite material. In addition, housing 50 and release mechanism 54 may be constructed of different materials instead of being constructed out of the same material. In some examples, housing 52 and/or release mechanism 54 may include a rubber or soft tactile surface to increase the friction with a hand of the user and prevent the hand of the user from slipping during use. In some embodiments, housing 50 and release mechanism 54 may be assembled through snap fit connections, adhesives or mechanical fixation devices such as pins or screws.

Needle 62 may be constructed with a polymer or a metal. For example, needle 62 may be constructed of stainless steel, aluminum, an aluminum alloy, a titanium alloy, nitinol, or any other biocompatible material. In addition, the material used by needle 62 may be malleable (or "moldable") by the user to create a shape capable of accessing the target site for stimulation. For example, a user may manipulate needle 62 to define a substantially curvilinear shape to help traverse the needle around certain anatomical features of the patient, such as an ear, bones, nerves that should be avoided, and so forth. In any case, implant tool 50 may be constructed to be disposable or capable of being sterilized after use with patient 12.

FIG. 3B shows a top view of implant tool 50. Housing 52 has a rounded shape to fit comfortably within the hand of a user. Grip 56 of release mechanism 54 is shown near flange 60 of housing 52. Flange 60 defines slot 57, which is a substantially linear opening substantially conforming to the shape of needle 62. The user may push against grip 56 to move release mechanism 54 toward needle 62 along slot 57 until the release mechanism reaches the distal end 57A of the slot.

As shown in FIGS. 3A and 3B, implant tool 50 is configured so that the user may grasp housing 52 with a hand and uses a thumb to press against grip 56 of release mechanism 54. In other examples, grip 56 may be positioned at another location on housing 52 that limits the stress to the hand of the user. For example, grip 56 may be positioned further away from needle 62 or to one side of housing 52 instead of positioned along the midline of the housing, as shown in the embodiment of FIGS. 3A-3B. In any case, release mechanism 54 may slide along needle 62 to push the cannula off of the needle 62 or away from housing 52 or hold the cannula 68 substantially in place relative to a target tissue site within patient 12 as needle 62 is withdrawn from the cannula. That is, when cannula 68 is subject to resistive forces (e.g., from surrounding tissue) that inhibit movement of cannula 68, release mechanism 54 essentially holds cannula 68 substantially in place as needle 62 is withdrawn, although the force applied by release mechanism 54 to cannula 58 is a pushing force away from housing 52.

Figure 4A:
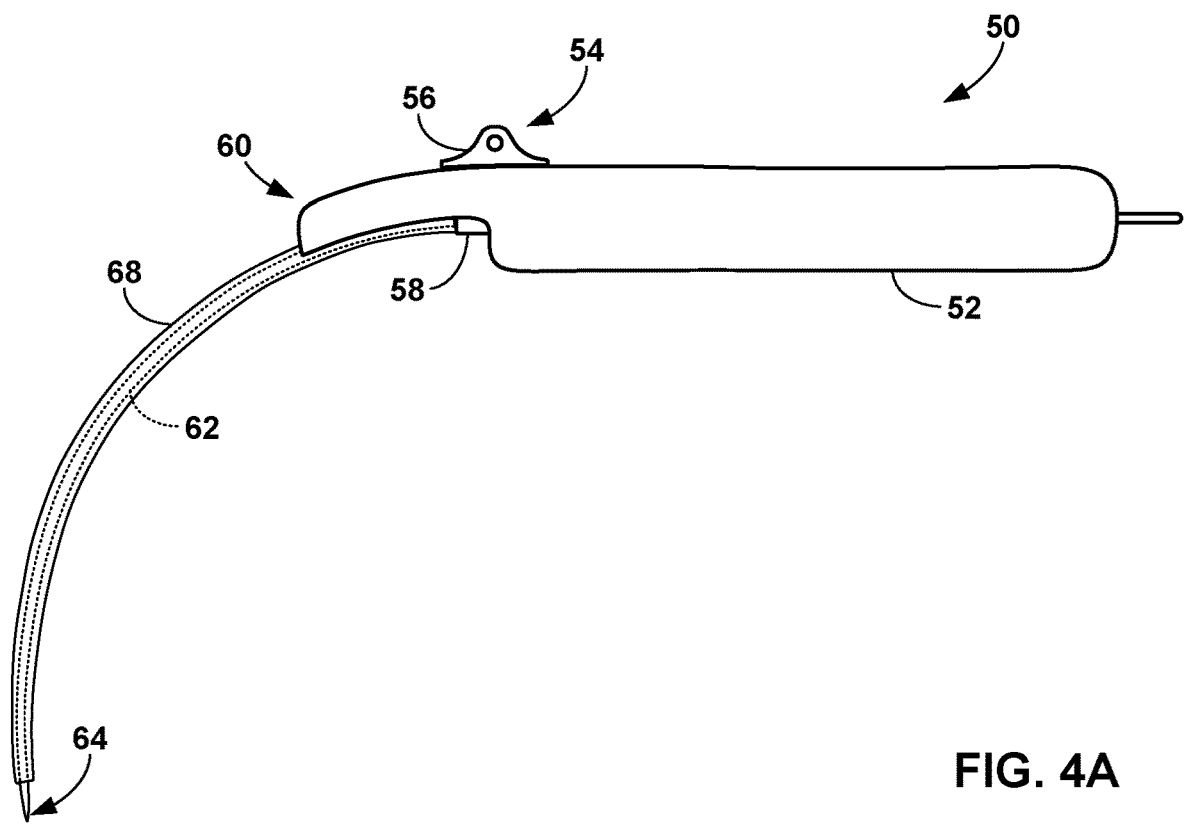
FIGS. 4A and 4B are side and bottom views, respectively, of an example implant tool having a release mechanism and a cannula.
Figure 4B:
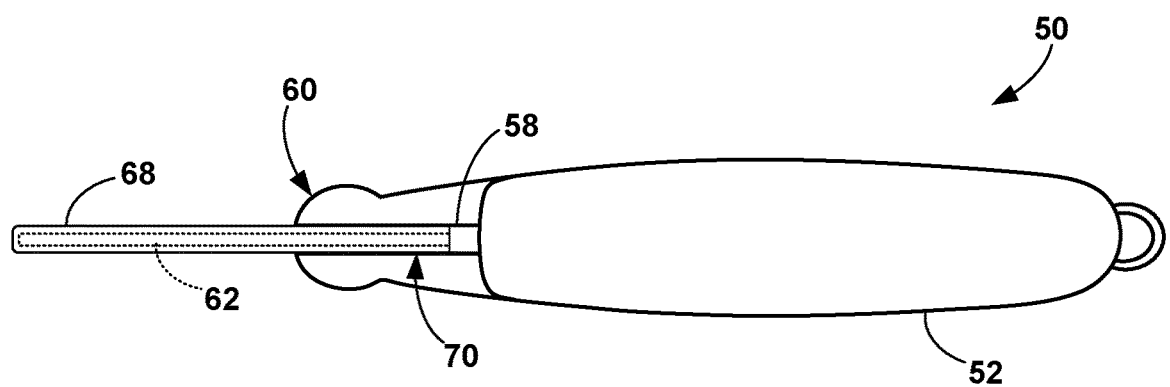

FIGS. 4A and 4B are side and bottom views, respectively, of example implant tool 50 including a release mechanism 54 and cannula 68. As shown in FIG. 4A, implant tool 50 includes cannula 68 fitted over needle 62 and substantially conforming to the shape of the needle. The length of cannula 68 is shorter than the exposed length of needle 62 to allow piercing tip 64 to extend past the end of the cannula. In this manner, piercing tip 64 defines an insertion path for needle 62 and cannula 68 through tissue of patient 12.

Cannula 68 is fitted over needle 62 and the proximal end of the cannula resides against guide 58 of release mechanism 54. In some embodiments, cannula 68 also rests against flange 60. However, in other embodiments, flange 60 does not contact cannula 68 until the user manipulates implant tool 50 such that cannula 68 flexes toward flange 60 and contacts flange 60. Flange 60 transmits force from housing 52 to cannula 68 and needle 62 to allow the user to push piercing tip 64 through tissue of patient 12 and minimize unwanted flexing of the needle. In some examples, flange 60 may resides around a greater surface area of cannula 68 to support forces in multiple directions from the user. Once the distal end of cannula 68 is positioned adjacent to the target site, the user pushes against release mechanism 54 to move the cannula off of needle 62 while withdrawing the needle from the cannula with housing 52. In this manner, release mechanism 54 allows the user to keep cannula 68 stationary with respect to patient 12 while removing needle 62 from the patient. While the user may use release mechanism to remove needle 62 from cannula 68 with only one hand, some users may prefer to use a second hand to stabilize the cannula while removing the needle.

FIG. 4B shows the bottom view of implant tool 50. In the embodiment shown in FIG. 4B, cannula 68 resides over needle 62 and adjacent to channel 70 defined by flange 60 and guide 58. In some embodiments, cannula 68 may fill the space between channel 70 and needle 62 in order to transmit force from flange 60 into the needle. Guide 58 of release mechanism 54 meets the proximal end of cannula 68 to facilitate the removal of the cannula from needle 62. In some examples, cannula 68 may extend into housing 52 if a longer cannula is desired for implantation of the medical device.

Cannula 68 may be constructed of a biocompatible material that is flexible to bend according to the shape of needle 62. Suitable materials may include polymers such as polyurethane, polyethylene, vinyl, expanded-polytetrafluoroethylene (ePTFE), or other polymers. Alternatively, cannula 68 may be constructed of a material that has a shape memory so that the cannula forms to a predetermined shape once removed from needle 62. Examples of suitable shape memory materials include, but are not limited to, a copper-zinc-aluminium alloy, copper-aluminium-nickel alloy, a nickel-titanium alloy (e.g., Nitinol) or ethylene tetrafluoroethylene (ETFE). Cannula 68 may be constructed of other plastics capable of being thermoset, or heated to a certain shape. Nitinol may provide an additional benefit in that it may be more readily visualized during fluoroscopy.

Figure 5A:
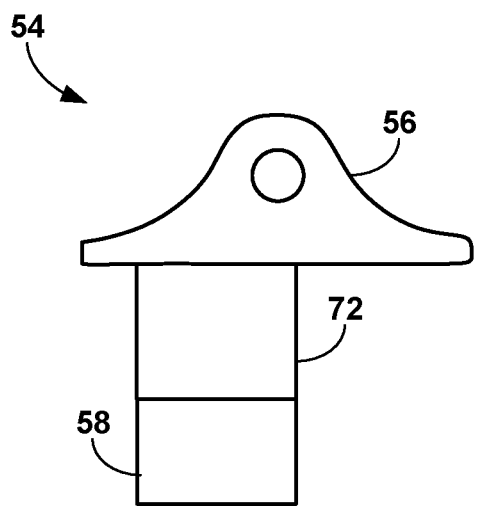
FIGS. 5A and 5B are side and front view, respectfully, of an example release mechanism for an implant tool.
Figure 5B:
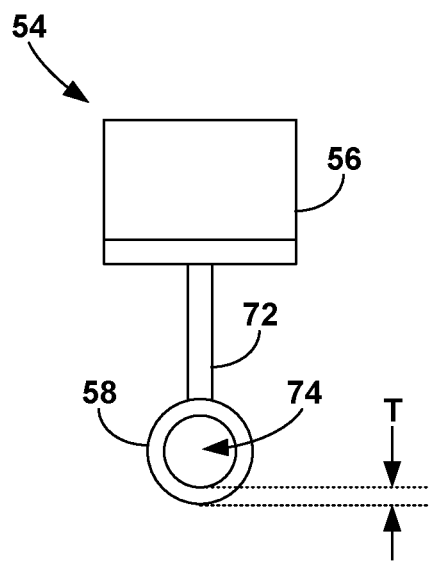

FIGS. 5A and 5B are side and front view, respectfully, of an embodiment of a release mechanism for an implant tool. As shown in FIG. 5A, release mechanism 54 of implant tool 50 includes grip 56 and guide 58 connected by member 72. Grip 56 is shaped with a substantially curved ramp on opposite sides of the grip to provide an ergonomic surface for engaging with release mechanism 54. Each curved ramp meets at the top of grip 56 and forms a substantially rounded apex. The bottom of grip 56 is generally flat; however, the bottom of the grip may be curved to match the curvature of housing 52 or flange 60. Member 72 is attached to the bottom of grip 56 and the top of guide 58, and shaped to provide rigidity between the grip and guide. Member 72 may or may not be resistant to bending forces due to the thin dimension of the member to fit within slot 57. Member 72 is also shaped to slide within slot 57 of housing 52.

FIG. 5B shows a front view of release mechanism 54. Grip 56 is sized to provide a sufficient surface area to contact the hand of the user. Member 72 has a narrow width that is sized to allow the member to slide within slot 57 of housing 52. In addition, guide 58 is shaped as a cylinder that defines channel 74. Channel 74 is shaped and sized to fit around the outer circumference of needle 62 such that the channel may slide along the needle. The wall thickness T of guide 58 may be substantially similar to the wall thickness of cannula 68 to push the end of the cannula. In some examples, guide 58 may only be semi-circular in shape such that the guide does not surround the entire needle 62.

Figure 6A:
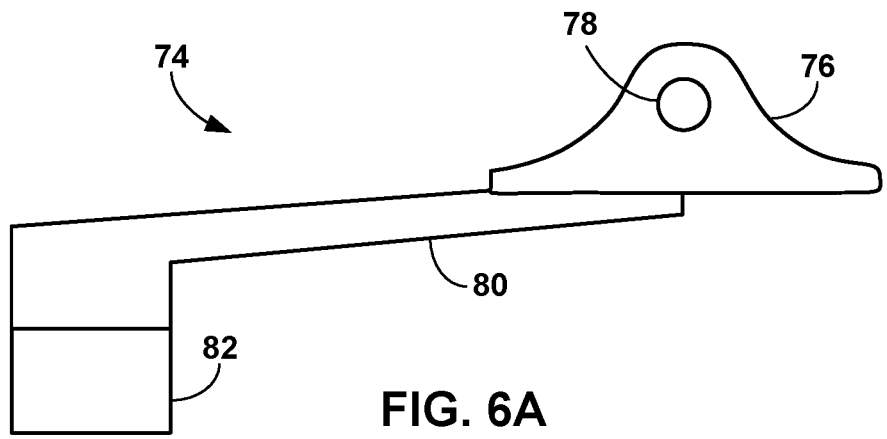
FIGS. 6A and 6B are side views of an example release mechanism of an implant tool.

FIG. 6A is a side view of another embodiment of a release mechanism of an implant tool. As shown in FIG. 6A, release mechanism 74 is substantially similar to release mechanism 54. However, release mechanism 74 is shaped to allow grip 76 to be positioned further from flange 60 of implant tool 50. The position of grip 76 located further from the needle of the implant tool may allow the user more leverage to push against the grip, which may be especially useful for users with small hands. In some examples, the position of grip 76 relative to flange 60 may be adjustable to the desires of the user.

Figure 6B:
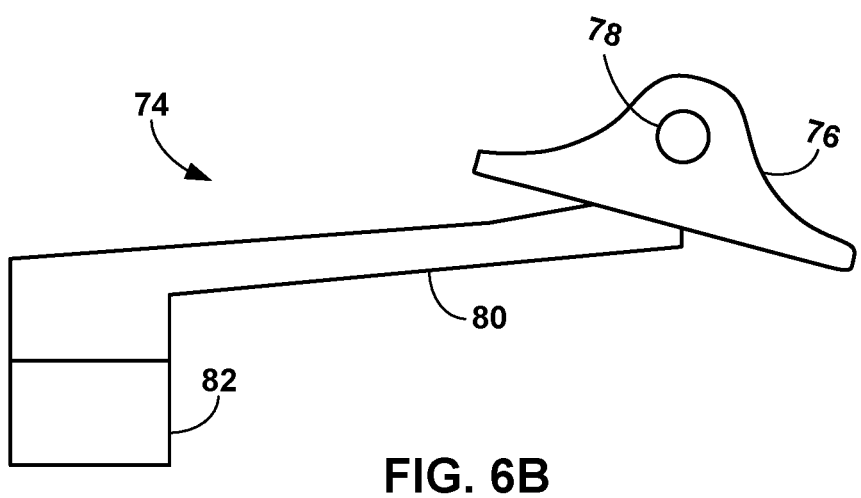

Grip 76 is attached to guide 82 via member 80. Member 80 is elongated and coupled to grip 76 with pivot pin 78. Pivot pin 78 allows grip 76 to pivot in the plane of member 80 such that guide 82 may follow the shape of needle 62 while the grip remains seated against housing 52. FIG. 6B shows grip 76 that has rotated about pivot pin 78. In this manner, the shape of needle 62 does not need to follow the shape of housing 52. In other examples, pivot pin 78 may define multiple pivot points or a ball joint to allow multiple degrees of freedom so that guide 82 may follow any bend or shape of needle 62 when moving cannula 68 off of the needle. Other examples of release mechanisms may be similar to those described herein and perform the similar function of moving cannula 68 off of needle 62.

Figure 7A:
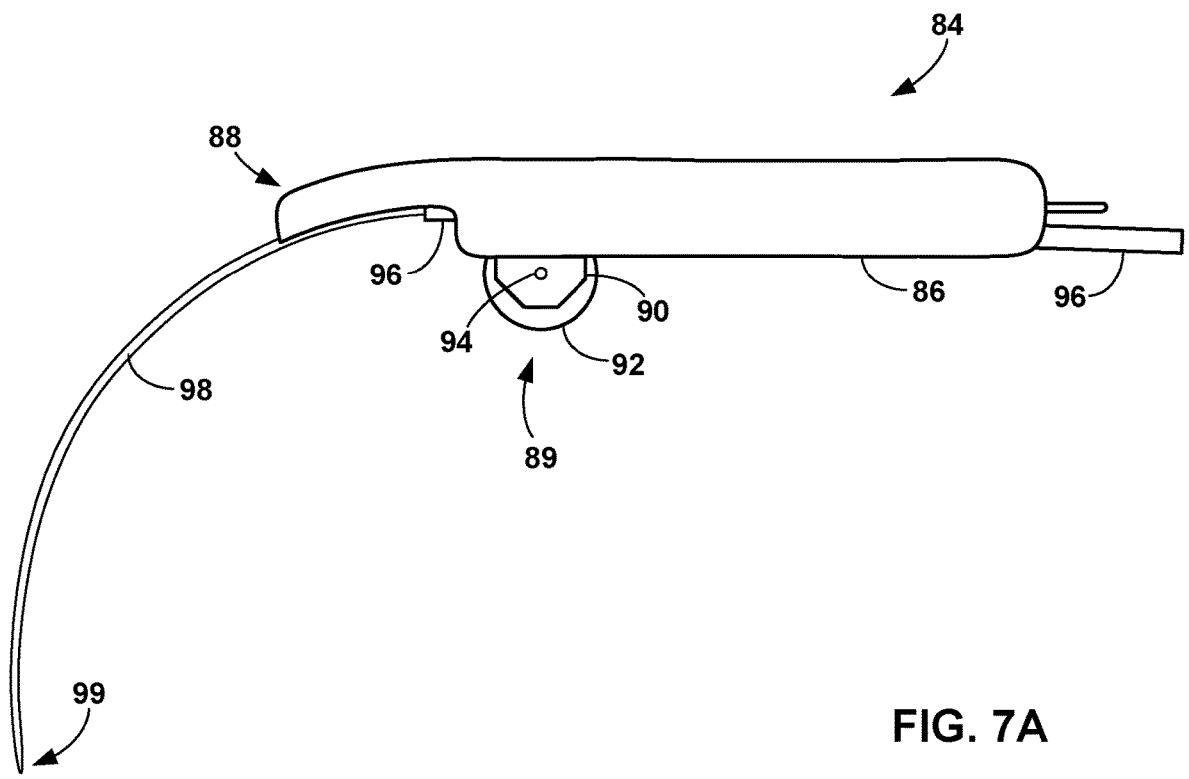
FIGS. 7A and 7B are side and bottom views, respectfully, of an example implant tool with a release mechanism having a pushing member and a wheel.
Figure 7B:
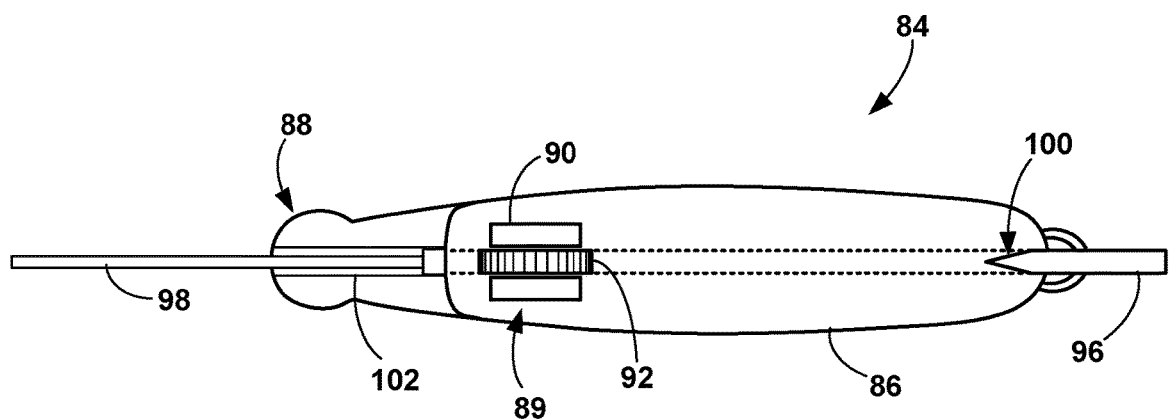

FIGS. 7A and 7B are side and bottom views, respectfully, of an example implant tool with a release mechanism having a pushing member and wheel assembly. Implant tool 84 is similar to implant tool 50, except that implant tool 84 includes a rotating release mechanism. As shown in FIG. 7A, implant tool 84 includes housing 86, needle 98, and release mechanism 89. Needle 98 resides within a channel defined by housing 86 and has piercing tip 99 and a shape conducive for defining an insertion path through tissue to access the target site within patient 12 via an external tissue opening, and in some embodiments, needle 98 is malleable. Release mechanism 89 is coupled to housing 86 and includes mounts 90, wheel 92, axle 94, and pushing member 96 that allows a user to force a cannula (not shown) off of needle 98.

Implant tool 84 may be configured to be held in a hand of a user. As with housing 52, housing 86 may have a shape that is relatively simple to construct and/or a shape that is ergonomically formed to rest within a human hand. Housing 86 may be constructed of substantial stiffness to resist flexing during use by the user. In addition, housing 86 defines a channel within the housing that secures needle 98 to the housing. The channel may have two or more segments which reside on two sides of housing 86 to resist twisting torque applied to needle 98 from the user. Specifically, needle 98 may form a loop that matches a loop-shaped channel within housing 86 that secures the needle within the housing. Housing 86 also defines a slot that allows release mechanism to slide along the proximal portion of needle 98.

Housing 86 is also shaped to transmit force from the hand of the user to piercing tip 99 of needle 98. Housing 86 includes flange 88 positioned along one side of needle 98 that supports needle 98 when the user attempts to push piercing tip 99 through tissue of patient 12. Flange 88 is substantially similar to flange 60 of implant tool 50 (FIG. 3A). In some embodiments, flange 88 may define a semicircular channel that follows along the length of needle 98 to spread out the force over a greater surface area of the needle. A space between the channel of flange 88 and needle 98 may allow the wall of a cannula to fit between the flange and the needle. In some examples, flange 88 may be shaped to surround a greater or lesser portion of needle 98. In other examples, flange 88 may completely surround needle 98 to support movements of the needle in any direction within patient 12 when introducing the needle into tissue of the patient.

Pushing member 96 is sized to receive needle 98, such that pushing member 96 may be moved relative to needle 98. In one embodiment, pushing member 96 slides along an outer surface of needle 98. Release mechanism 89 includes mounts 90, wheel 92, axle 94, and pushing member 96. Release mechanism 89 is configured to apply force against the end of a cannula in a direction substantially towards piercing tip 99 of needle 98 or otherwise away from housing 86. The user may rotate wheel counterclockwise with a thumb or a finger to move pushing member 96 along needle 98 towards piercing tip 99. In turn, the pushing member 96, which at least partially surrounds needle 98, helps initiate relative movement between the cannula and needle 98, such as by forcing the cannula off of needle 98. In this manner, the user may withdraw needle 98 from the cannula while keeping the cannula substantially stationary relative to patient 12. Pushing member 96 slides within a member channel within housing 86 and is pressed between wheel 92 and the housing so that the friction between the wheel and the pushing member is great enough to move the pushing member.

In some examples, wheel 92 and/or pushing member 96 may have ridges, bumps, or teeth that aid in the friction between the wheel and the pushing member. In other examples, wheel 92 may ratchet against housing 86, mounts 90, or axle 94 to only allow counterclockwise movement of the wheel until the cannula is moved off of needle 98. Alternatively, pushing member 96 may ratchet within the member channel (not shown) of housing 86 to only allow unidirectional movement of the pushing member. The user may need to fully remove pushing member 96 from housing 86 and reinsert the pushing member into the housing to re-use the pushing member with implant tool 84.

Housing 86 and release mechanism 89 may be constructed of a variety of materials, such as a lightweight molded plastic, e.g., polystyrene. In other embodiments, other injection molded plastics may be used such as polyurethane, polypropylene, high molecular weight polyurethane, polycarbonate or nylon. Alternatively, construction materials may include aluminum, stainless steel, a metal alloy or a composite material. In addition, housing 86 and release mechanism 89 may be constructed of different materials instead of being constructed out of the same material. In some examples, housing 86 and/or release mechanism 89 may include a rubber or soft tactile surface to prevent the hand of the user from slipping during use. In some embodiments, housing 86 and release mechanism 89 may be assembled through snap fit connections, adhesives or mechanical fixation devices such as pins or screws.

Needle 98 may be constructed with a polymer or a metal, similar to needle 62. For example, needle 98 may be constructed of stainless steel, aluminum, an aluminum alloy, a titanium alloy, nitinol, or any other biocompatible material. In addition, the material used by needle 98 be malleable by the user to create a shape capable of accessing the target site for stimulation. In any case, implant tool 84 may be constructed to be disposable or capable of being sterilized after use with patient 12.

FIG. 7B shows a bottom view of implant tool 84. Housing 86 has a rounded shape to fit comfortably within the hand of a user while inserting needle 98 into patient 12. Pushing member 96 resides within member channel 100 of housing 86 and exits the housing against needle 98 near flange 88. Wheel 92 contacts pushing member 96 through an opening in housing 86 (not shown) adjacent to the wheel, and the wheel may have ridges along the outside edge of the wheel. Wheel 92 is rotated by the user to move pushing member 96 along needle 98 until cannula is removed from the needle or the pushing member can no longer be advanced by the wheel. Flange 88 also defines channel 102 that creates a space between the flange and needle 98 to accept the cannula and promote the transfer of force from the flange to the needle during insertion into patient 12.

As shown in FIGS. 7A and 7B, implant tool 84 is configured so that the user grasps housing 86 with a hand and uses their thumb or finger to rotate wheel 92 of release mechanism 89. In other examples, wheel 92 may be positioned at another location on housing 86 that limits the stress to the hand of the user. For example, wheel 92 may be positioned further away from needle 98 or to one side of housing 86 instead of positioned along the midline of the housing bottom. In any case, release mechanism 89 may be used to move the cannula along needle 98 and off of the needle.

Figure 8A:
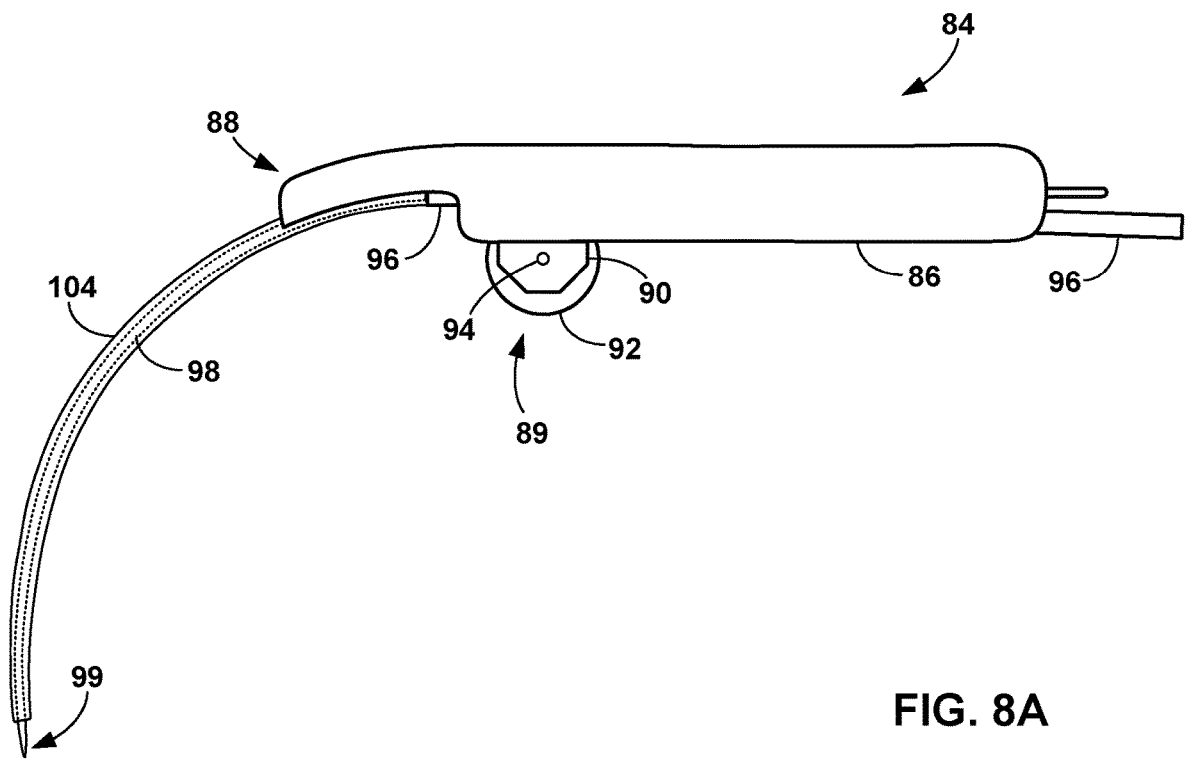
FIGS. 8A and 8B are side and bottom views, respectfully, of an example implant tool with a release mechanism having a pushing member and a wheel to move a cannula.
Figure 8B:
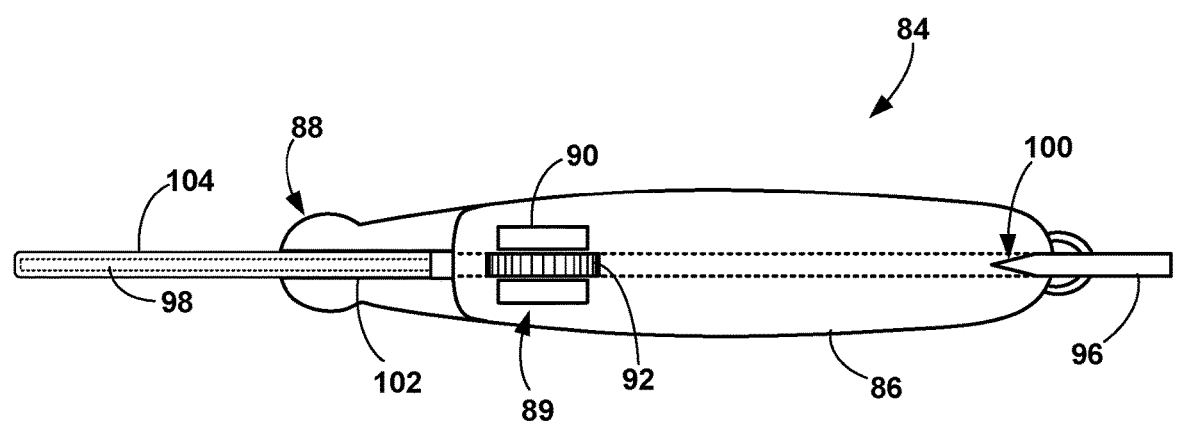

FIGS. 8A and 8B are side and bottom views, respectfully, of an example implant tool with a release mechanism including a pushing member and wheel assembly to move a cannula. Cannula 104 is substantially similar to cannula 68 of FIGS. 4A and 4B. As shown in FIG. 8A, implant tool 84 includes cannula 104 fitted over at least a portion of needle 98 and substantially conforming to the shape of the needle. The length of cannula 104 is slightly shorter than the exposed length of needle 98 to allow piercing tip 99 to extend past the distal end of the cannula 104. In this manner, piercing tip 99 of needle 98 may define an insertion path through tissue for needle 98 and cannula 104.

Cannula 104 is fitted over needle 98 and the proximal end of the cannula resides against pushing member 96 of release mechanism 89. Cannula 104 also rests against flange 88 and is disposed between needle 98 and flange 88. Flange 88 transmits force from housing 86 to cannula 104 and needle 98 to allow the user to apply a force to push piercing tip 99 through tissue of patient 12 and minimize unwanted flexing of the needle. In some examples, flange 88 may reside around a greater surface area of cannula 104 to support forces in multiple directions from the user. Once the distal end of cannula 104 is positioned adjacent to the target site, the user rotates wheel 92 to move pushing member 96 against the cannula. In this manner, the user may initiate relative movement between cannula 104 and needle 98 in order to withdraw the needle from the cannula while substantially holding cannula 104 in place relative to the target tissue site.

In alternative embodiments, release mechanism 89 may not require pushing member 96 to move cannula 104 with respect to needle 98. Instead, cannula 104 may extend along needle 98 within housing 86 and be positioned next to wheel 92. Rotation of wheel 92 may directly contact the outside surface of cannula 104 and move the cannula along needle 98. In this manner, the user may have direct control of the release of cannula 104 from implant tool 84.

FIG. 8A shows the bottom side of implant tool 84. Cannula 104 is shown as residing over needle 98 and adjacent to channel 102 of flange 88 and the distal end of pushing member 96. Cannula 104 may fill the space between channel 102 and needle 98 in order to transmit force from flange 88 into the needle. Pushing member 96 of release mechanism 89 meets the proximal end of cannula 104 to facilitate the removal of the cannula from needle 98. In some examples, cannula 104 may extend to a position within housing 86 if a longer cannula is needed for implantation of the medical device.

Implant tools 50 or 84 may employ alternative release mechanisms not described herein but perform similar functions for substantially holding a cannula in place proximate to a target tissue site within a patient while initiating relative movement between a cannula and a needle. Other release mechanisms may include ratcheting mechanisms that allow the user to move the cannula in one direction and prevent the user from retracting the cannula towards the housing. For example, the user may push a cradle against a pushing member to force the cannula off of the needle. The cradle may have angled teeth that lock against teeth of the pushing member when the cradle moves toward the needle. The user may then pull the cradle back away from the needle as the teeth of the cradle and pushing member slide over each other. Additional movements of the cradle toward the needle may continue to move the pushing member against the cannula.

Figure 9:
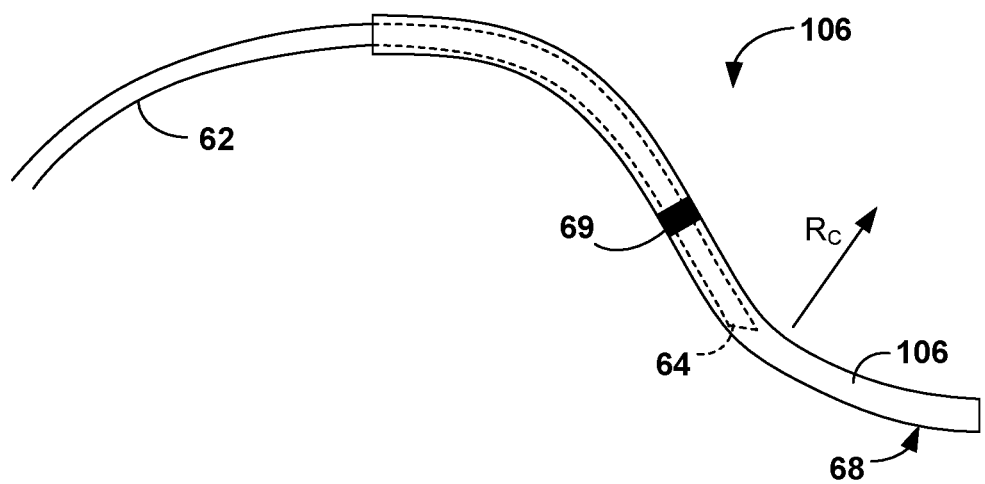
FIG. 9 is an illustration of a cannula having a shape memory partially over a needle.

FIG. 9 is an illustration of cannula 68 having a shape memory being removed from needle 62. While cannula 68 and implant tool 50 are described in FIG. 9, other cannulas, such as cannula 104 (FIGS. 8A-8B), and implant tools, such as implant tool 84 (FIGS. 7A-8B), may be similar in function and structure. As shown in FIG. 9, as needle 62 is removed from lumen 106 of cannula 68, cannula 68 changes conformation to a shape of radius $R_C$. The shape may aid in directing a distal tip of a medical lead, catheter or another medical device to an appropriate target tissue site. In one embodiment, cannula 68 defines the shape prior to implantation within patient 12, but adapts to the shape of needle 62 while needle 62 is disposed within cannula 68 because needle 62 is typically more rigid than cannula 68. Upon withdrawal of needle 62, cannula 68 assumes the shape defined by $R_C$, which has a radius of curvature $R_C$. $R_C$ may vary due to patient anatomy or the tissue targeted to be stimulated. In general, $R_C$ is in a range of approximately 1 cm to 20 cm. More preferably, $R_C$ is in a range of approximately 2 cm to 10 cm. As needle 62 is completely removed from cannula 68, cannula 68 achieves the shape shown in FIG. 9. A medical device may then be introduced into the inner lumen of cannula 68 previously occupied by needle 62 of implant tool 50.

Cannula 68 may include an additional visible marker 69 to indicate the direction in which cannula 68 is configured to curve. Marker 69 enables the clinician to orient implant tool 50 during implantation in the patient such that when needle 62 is removed from the lumen of cannula 68, cannula 68 curves in the desired direction. In some embodiments, marker 69 is in a location in which marker 69 remains visible to the clinician after the clinician introduces implant tool 50 into patient 12. For example, marker 69 may be positioned on needle 62 in addition to or instead of on cannula 68. In general, marker 69 may be located anywhere on tool 50, so long as marker provides the clinician with enough information to determine which direction cannula 68 will curve.

Cannula 68 may also help refine the shape of the insertion path previously defined by needle 62. In some cases, needle 62 may not be able completely define the desired insertion path because the shape (i.e., configuration) of needle 62 is dictated by the shape that is necessary to reach the target tissue site without causing substantial damage to tissue. For example, in some embodiments, it may be desirable for a deep portion of the insertion path (i.e., the portion furthest from the entry point) to pivot or curve about 30 degrees or more. However, it may be undesirable for the distal portion of needle 62 to pivot about 30 degrees or more because such a needle may be difficult to guide through tissue of the patient without causing unnecessary trauma to the tissue. Cannula 68, on the other hand, may provide the pivot or curve after being tunneled through the tissue.

The pivot or curve at the end of the insertion path may be useful for implanting a lead, catheter or another elongated medical device to be implanted with extra slack in order to impart strain relief to the implanted elongated medical device. That is, upon changing shape after the removal of needle 62, cannula 68 may refine the insertion path to include a greater curvature than that achieved by needle 62, which allows an elongated medical device to be implanted such that the elongated member has a greater length than necessary to reach the implant site of an electrical stimulator, fluid delivery device or another therapy device to be implanted. The greater length of the elongated medical device may help the medical device withstand pulling forces attributable to the movement of muscles along the path traversed by the elongated medical device. The shape memory aspect of cannula 68 may also aid in the implantation of a medical device to regions within a patient that may be difficult to reach with needle 62, which may not be able to achieve to certain radii of curvature despite being malleable in some embodiments.

In addition to the shape memory material of cannula 68, a coating may also be applied to at least a part of cannula 68. For example, a parylene or oxide film coating may be applied to cannula 68 in order to electrically insulate the cannula. Also, addition of a lubricating film or coating, such as polytetrafluoroethylene (PTFE), to the outer surface of cannula 68 may be desirable to facilitate insertion.

Figure 10:
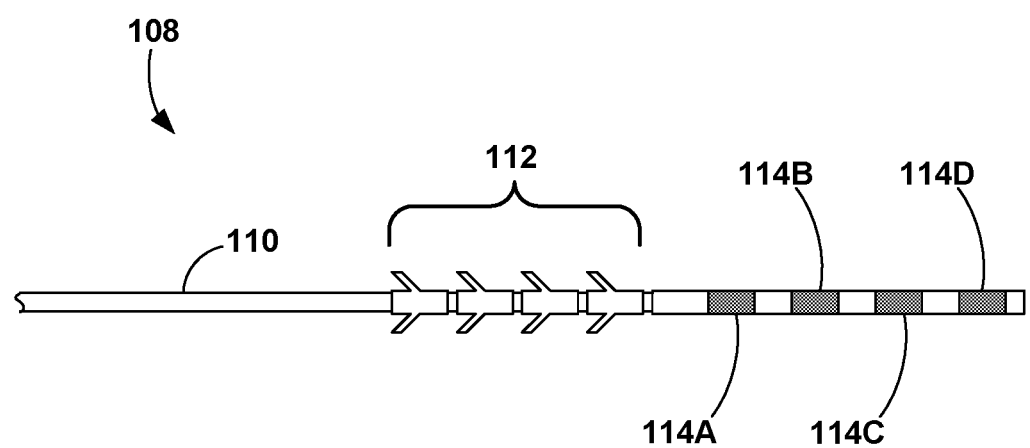
FIG. 10 is a side view of an example implantable medical lead capable of being implanted via the cannula.

FIG. 10 is a side view of an example implantable medical lead capable of being implanted via the cannula. As shown in FIG. 10, lead 108 is an example medical device that may be implanted using implant tool 50 and cannula 68, for example. Lead 108 includes lead body 110, tines 112, and electrodes 114A, 114B, 114C, and 114D (collectively "electrodes 114"). Electrodes 114 may be similar to electrodes 26 of FIG. 2A. After implant tool 50 is properly positioned relative to a target site within patient 12, and needle 62 is withdrawn from cannula 68, lead 108 may be advanced through the lumen of cannula 68 until electrodes 114 are properly placed relative to the target site. Implant tool 50 may also be used to tunnel the proximal end of lead 108 (not shown) to the location that stimulator 14 resides patient 12.

When the user removes cannula 68 from around lead 108, tines 112 unfold and extend into the surrounding tissue to anchor or fix the position of electrodes 114 relative to the target tissue site. In other examples, lead 108 may utilize less or more tines anywhere along lead housing 110. In alternative examples, lead 108 may include fixation elements different than leads 112. For example, lead 108 may incorporate any of helical fixation elements, snap closure elements, hydrogel elements, tissue adhesives, or sutures to anchor the lead within patient 12.

Figure 11:
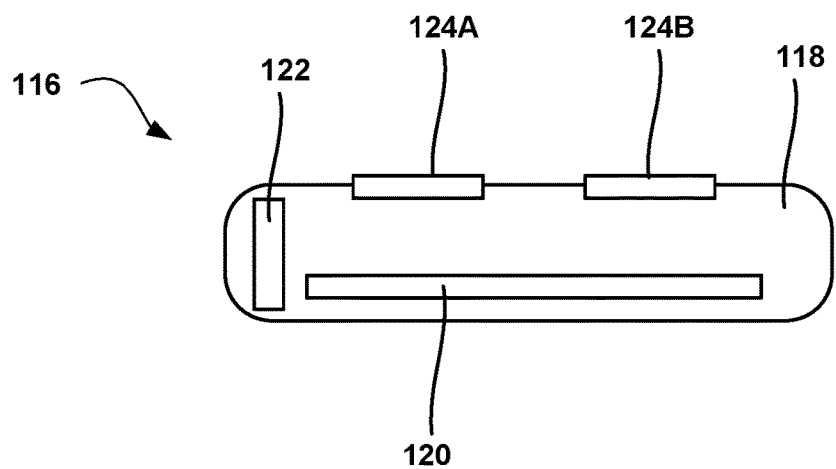
FIG. 11 is a block diagram of an example implantable medical device capable of being implanted via the cannula.

FIG. 11 is a block diagram of an example leadless medical device capable of being implanted via the cannula. Implant tool 50 or 84 and cannulas 68 or 104, respectively, may also be used to directly implant a leadless electrical stimulation module 116 within patient 12. Stimulation module 116 may be appropriate at sites where leads are not desired or stimulation is desired at multiple locations in a certain region. Stimulation module 116 may provide leadless electrical stimulation using a unitary, integrated stimulation module carrying one or more electrodes, stimulation pulse generation circuitry, and optionally telemetry circuitry. FIG. 11 is a schematic diagram illustrating an exemplary leadless electrical stimulation module 116 for electrical stimulation of a target site within patient 12. Stimulation module 116 may be implanted using implant tool 50 or 84 and the respective cannula 68 and 104.

Stimulation module 116 includes implantable housing 118, circuit board 120, power supply 122, and electrodes 124A and 124B (collectively "electrodes 124"). Stimulation module 116 contains all necessary components to provide complete stimulation therapy without any lead or other wire connected to stimulation module 116. Stimulation module 116 may be implanted using devices and techniques as described in this disclosure.

Housing 118 is biocompatible and protects the components of stimulation module 116 from corrosive biological fluids and tissues. Housing 118 may contain fixation mechanisms, such as tines similar to tines 112 of lead 108 to secure stimulation module 116 near a desired nerve location. Circuit board 120 includes components such as a processor, memory, telemetry circuitry, or other electronics necessary for performing electrical stimulation, similar to the components of stimulator 14A shown in FIG. 2A. Power source 122 includes a battery or rechargeable battery to power the electrical circuitry of stimulation module 116. Power source 122 may also generate power through a trickle charger utilizing patient motion or induction with an external device. Electrodes 124 are attached to housing 118 and may be either a cathode or anode to provide electrical stimulation. In some embodiments, stimulation module 116 may include more than two electrodes. Alternatively, electrodes 124 may be tethered to housing 116 with a lead. In some embodiments, multiple leadless stimulation modules 116 may be implanted within the pelvic floor using devices and techniques as described in this disclosure.

Figure 12:
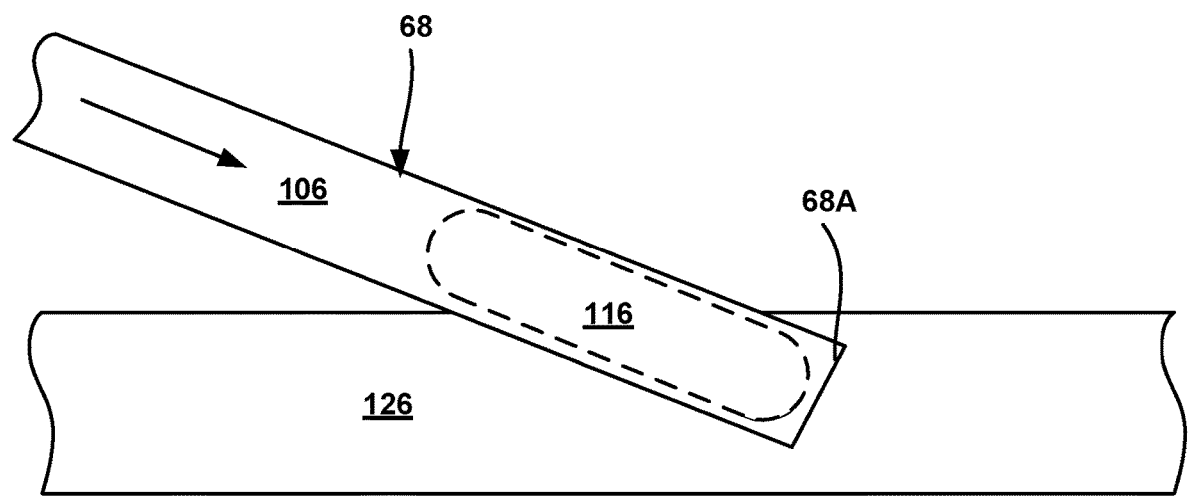
FIG. 12 is an illustration of an example implantable medical device being implanted into a tissue site via the cannula.

FIG. 12 is an illustration of an example implantable medical device 116 being implanted into a tissue site 126 via the cannula 68. Tissue site 126 may be the pelvic floor as one example, and in other embodiments, leadless stimulation module 116 may be implanted proximate to a peripheral nerve of patient 12. A distal end 68A of cannula 68 has been positioned proximate to target tissue site 126 using, for example, implant tool 50. Inner lumen 106 of cannula 68 may be sized to receive module 116. Stimulation module 116 may be small enough to slide through inner lumen 106 of cannula 68, such that stimulation module 116 may be implanted proximate to target tissue site 126 within patient 12. That is, after distal end 68A of cannula 68 is positioned proximate to target tissue site 126 via implant tool 50 (or any other suitable implant tool), needle 62 may be withdrawn from inner lumen 106 of cannula 68. Thereafter, stimulation module 116 may be introduced into inner lumen 106 of cannula 68 to reach the target tissue site 126. In other embodiments, stimulation module 116 may be implanted through needle 62 without cannula 68. In some cases, a guide wire or stylet may be used to aid in placing stimulation module 116 in an appropriate location. In addition, in some cases, more than one stimulation module 116 may be placed adjacent to tissue site 126 for effective stimulation therapy.

Figure 13A:
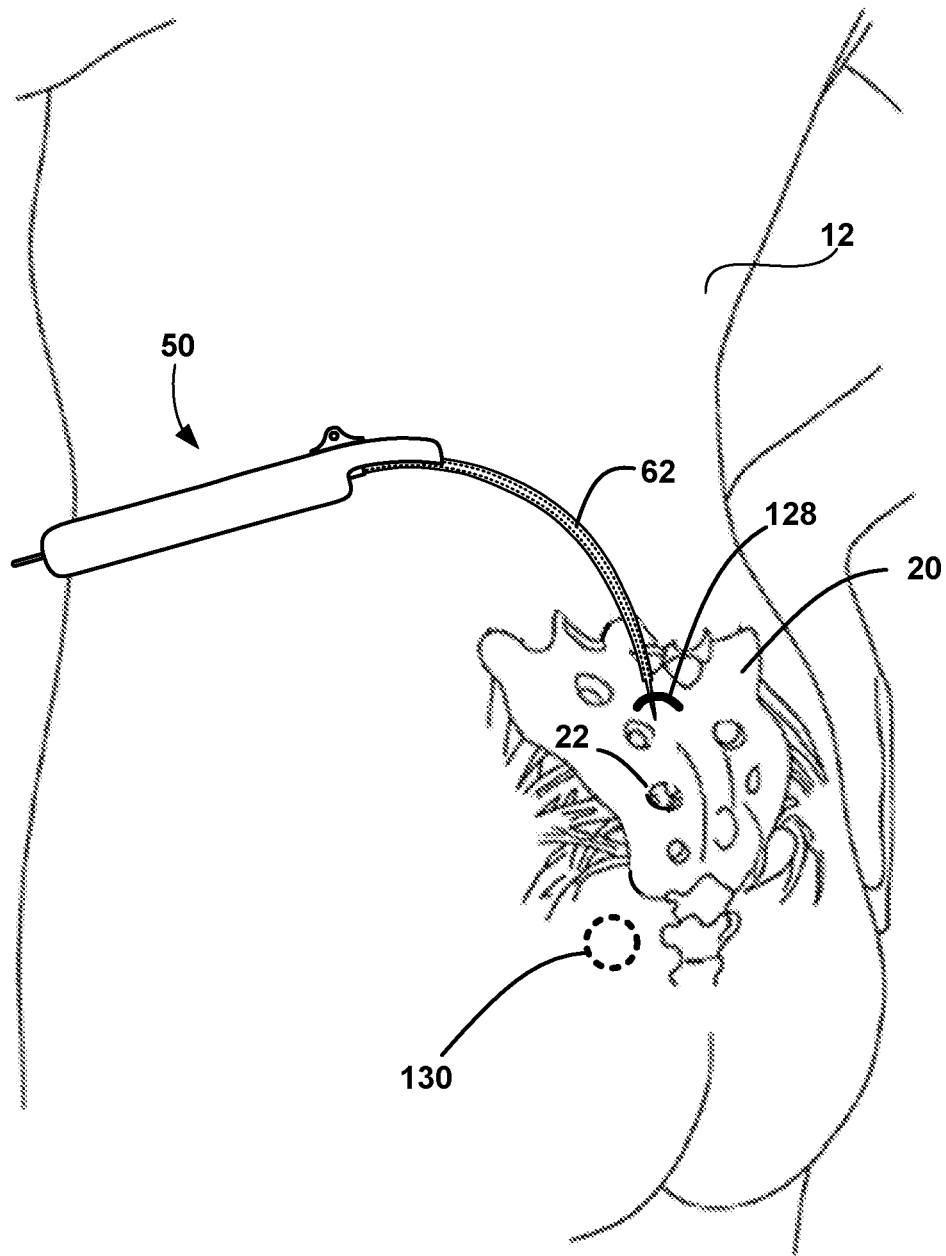
FIGS. 13A-13D are illustrations of an example technique for implanting a medical device using an implant tool with a release mechanism.

FIGS. 13A-13D are illustrations of an example technique for implanting a medical device using an implant tool with a release mechanism. Implant tool 50 and cannula 68 will be used in the example of FIGS. 13A-13D. However, other implant tools and cannulas such as implant tool 84 and cannula 104 (shown in FIGS. 7A-8B) may be similarly used. As shown in FIG. 13A, a user begins introducing needle 62 of implant tool 50 into patient 12 in order to implant a medical device at target site 130 within the pelvic floor of the patient. As one example, target site 130 may be adjacent to a sacral nerve to treat urinary incontinence. In other embodiments, target site 130 may be any suitable tissue site within patient 12, such as other nerves or muscles. Skin opening (or "entry point") 128, through which needle 62 is inserted, may be created by piercing tip 64 or by an incision made by the user. Skin opening 128 may be just large enough for needle 62 and cannula 68 to pass into patient 12 in order to minimize the invasiveness of the implantation procedure.

The user holds onto housing 52 of implant tool 50 to direct the insertion of needle 62 and cannula 68 into patient 12 via skin opening 128. Generally, the path of needle 62 and cannula 68 may be controlled by the shape of needle 62. The shape of needle 62 may be preformed based upon the implant location. Alternatively, needle 62 may be malleably, allowing the shape of needle 62 to be altered by the user during the implantation procedure as the need arises for needle 62 to achieve a different shape. In this way, a malleable needle 62 enables the user to personalize implant tool 50 the anatomy of a particular patient or to a particular target tissue site 130. The user may guide implant tool 50 along a path through tissue of patient 12 that substantially follows the shape of needle 62. In the embodiment shown in FIG. 13A, needle 62 and cannula 68 are guided through dorsal foramen 22 in sacrum 20 in order to access tissue site 130. In some cases, the user may use a second hand to help guide needle 62.

Figure 13B:
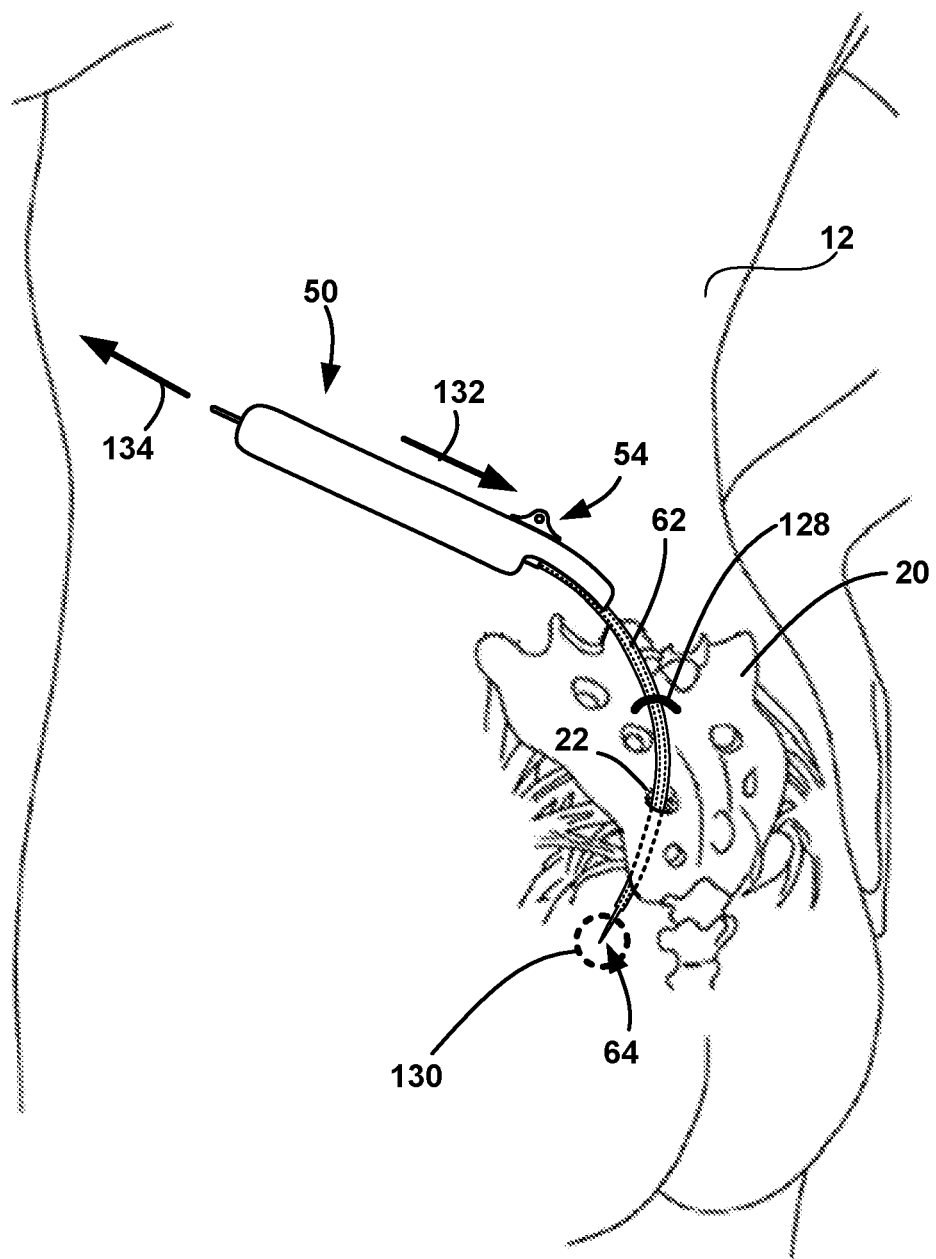

FIG. 13B shows the orientation of implant tool 50 relative to patient 12 when piercing tip 64 of needle 62 is correctly placed adjacent to target site 130. Needle 62 and cannula 68 extend through dorsal foramen 22 in sacrum 20 and out of patient 12 via skin opening 128. When removing implant tool 50 from cannula 68, it is typically undesirable to move the cannula with respect to patient 12 and target site 130 because the position of cannula 68 may affect the implant site for the medical device, which may ultimately affect the efficacy of therapy delivery to patient 12. Thus, in order to minimize movement of cannula 68 as needle 62 is withdrawn from patient 12, the user may push release mechanism 54 in the direction of arrow 132 while simultaneously pulling back on implant tool 50 in the direction of arrow 134. The user continues to withdraw implant tool 50 in the direction of arrow 134, and the direction of withdrawal of implant tool 50 may be influenced by the shape of needle 62. By applying a force to cannula 68 that substantially counteracts any forces imposed on cannula 68 from the withdrawal of implant tool 50, release mechanism 54 retains cannula 68 substantially in place adjacent to target site 130 during the withdrawal of needle 62 from the cannula.

Figure 13C:
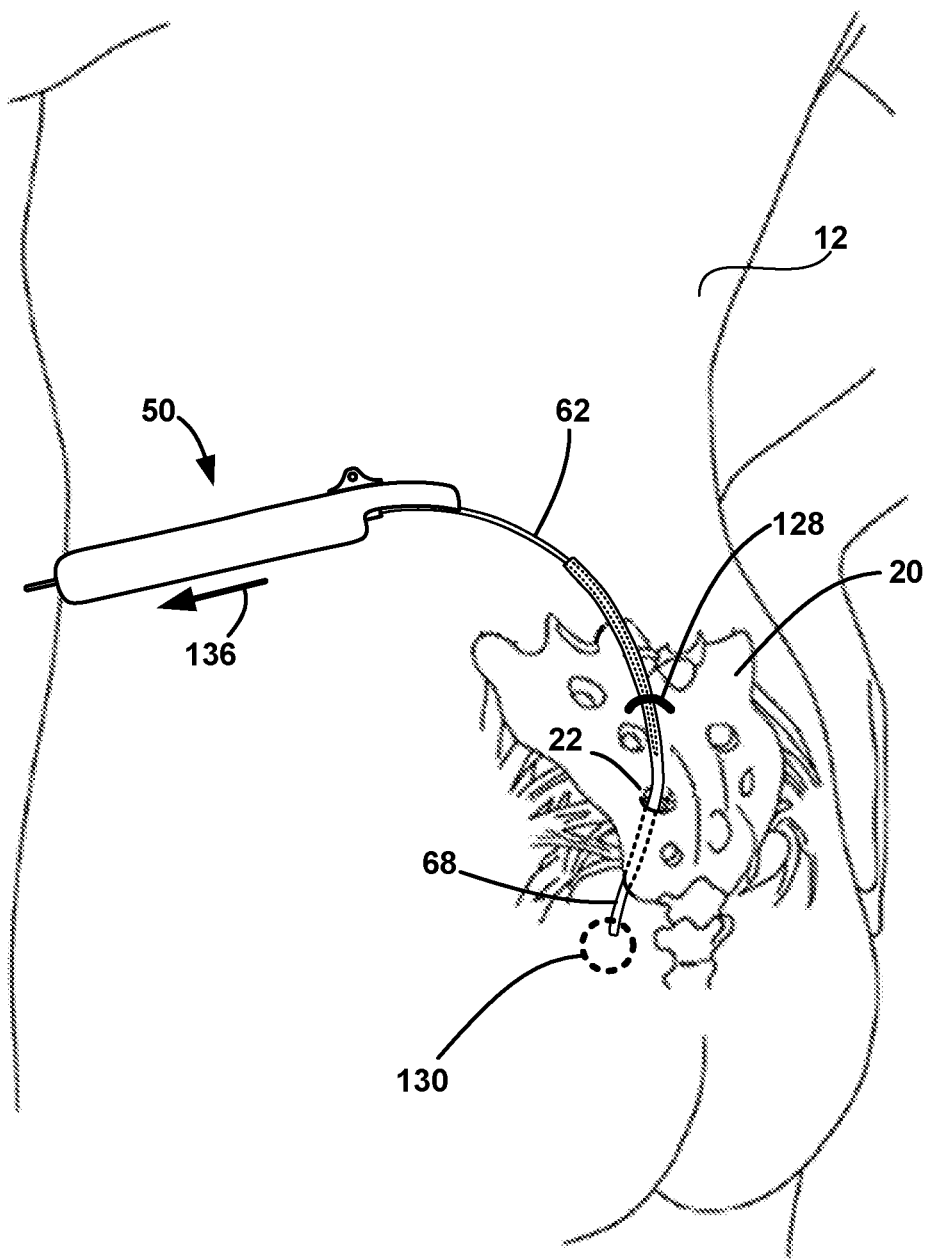

FIG. 13C shows implant tool 50 partially removed from cannula 68 and patient 12. The distal end of cannula 68 remains adjacent to target site 130 while needle 62 is moved in the direction of arrow 136. Since release mechanism 54 may not contact the proximal end of cannula 54 during the entire removal process, the user may hold onto housing 52 of implant tool 50 with one hand while grasping the proximal end of cannula 68 that remains outside of patient 12. In other implant techniques utilizing other embodiments of implant tools, the release mechanism may continue to engage cannula 68 until needle 62 has been completely removed from the cannula. As previously described, however, in some cases, movement of cannula 68 relative to target tissue site 130 when needle 62 is withdrawn from cannula 68 may be attributable to static friction between cannula 68 and needle 62. Accordingly, embodiments of implant tools in which release mechanism 54 engages with cannula 68 to hold cannula 68 substantially in place only during an initial step of initiating movement between cannula 68 and needle 62 may still be useful. After the withdrawal of implant tool 50 from cannula 68, the cannula remains within patient 12 and is ready to receive the medical device for implantation through inner lumen 106.

Figure 13D:
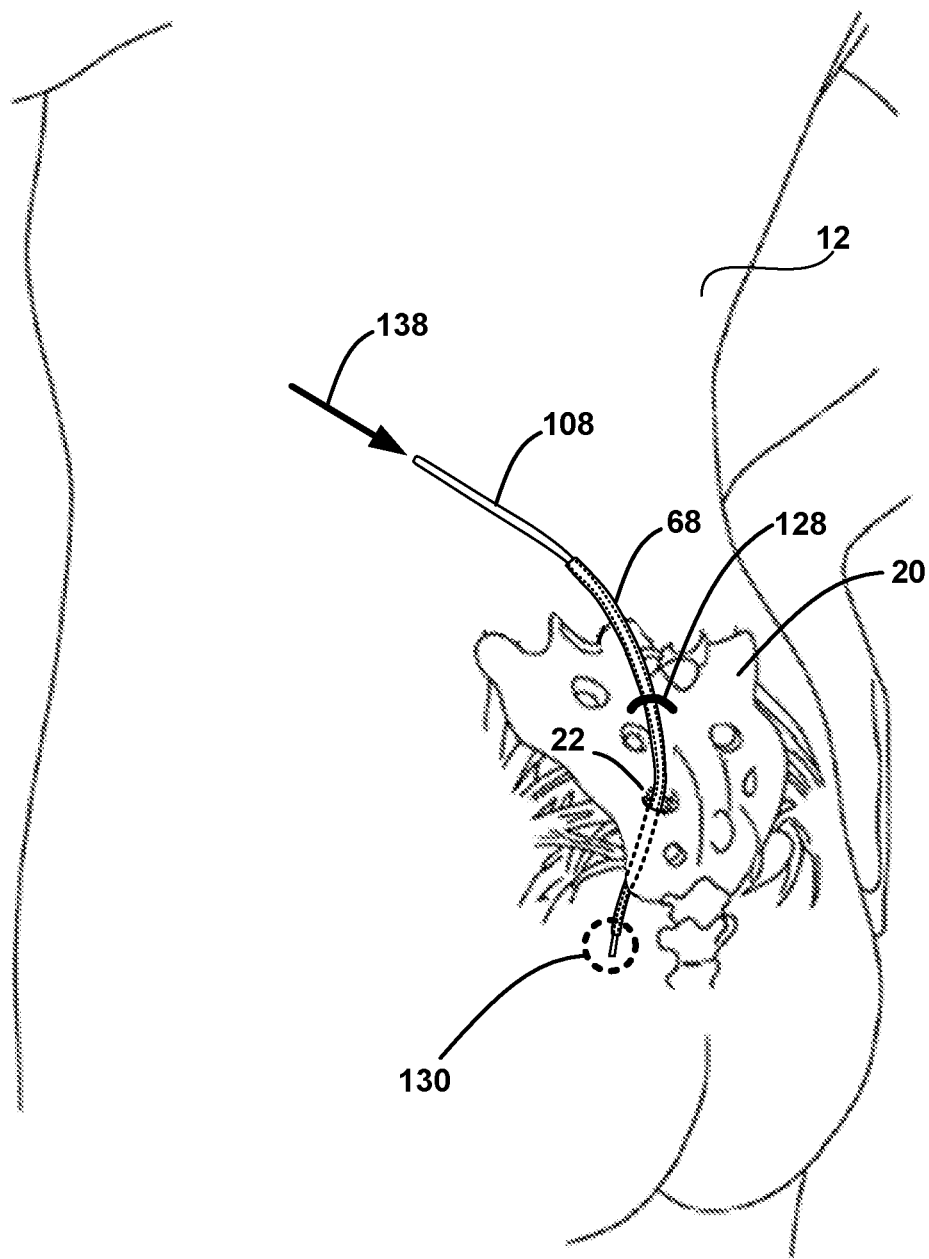

FIG. 13D illustrates the insertion of a medical device, e.g., lead 108, into lumen 106 of cannula 68. In one embodiment, the user may grasp cannula 68 with one hand and slowly advance the distal end of lead 108 into the cannula in the direction of arrow 138. The user continues to feed lead 108 into cannula 68 until electrodes 114 are correctly positioned in relation to target site 130. In some examples the user may couple lead 108 to a stimulator in order to deliver test stimulation to target site 130. The test stimulation may aid the user in correct placement of lead 108. Once lead 108 is correctly positioned, the user removes cannula 68 while keeping lead 108 in place within patient 12. Removal of cannula 68 deploys tines 112, or other fixation devices, into surrounding tissue, and tines 112 may expand and anchor the distal end of lead 108 adjacent to tissue site 130. In addition, the user may tunnel the proximal end of lead 108 to the location of implantable stimulator 14 using an implant tool, such as implant tool 50.

While lead 108 was implanted into patient 12 using implant tool 50 and cannula 68, other medical devices may be implanted using the technique described in FIGS. 13A-13D. For example, a microstimulator, e.g., leadless stimulation module 116, or a fluid delivery catheter may be inserted into cannula 68 and implanted adjacent to target site 130. Alternatively, cannula 68 may be used to implant multiple leads or devices at desired location within patient 12. In any case, the release mechanism of the implant tool may allow the user to more easily retain the position of the cannula adjacent to the target site.

Figure 14:
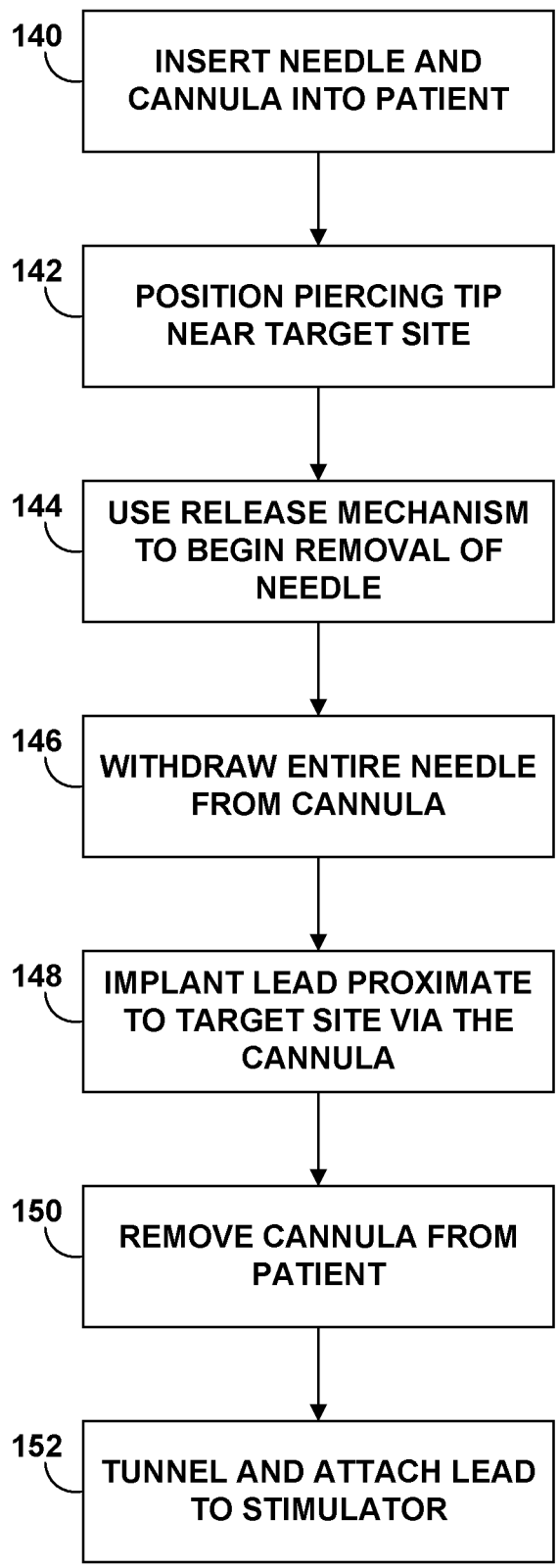
FIG. 14 is a flow diagram of an example technique for implanting a medical device using an implant tool.

FIG. 14 is a flow diagram of an example technique for implanting a medical device using an implant tool. Implant tool 50 and cannula 68 will be used in the example of FIG. 14. However, a similar technique may be used with implant tool 84 and cannula 104. As shown in FIG. 14, the user begins implantation by inserting cannula 68 into patient 12 through the use of needle 62 of implant tool 50 (140). The user continues inserting, or tunneling, needle 62 into patient 12 until piercing tip 64 of needle 62 is positioned near the target site (142). Once the user has positioned the distal end of cannula 68 correctly, the user uses release mechanism 54 to begin the removal of the cannula while simultaneously withdrawing needle 62 from the cannula (144). A technique for determining whether a distal end of cannula 68 is correctly positioned relative to a target tissue site is described below with reference to FIGS. 15-17.

The user continues to withdraw needle 62 from cannula 68 until the entire needle exits the cannula (146). With cannula in place, the user begins to feed lead 108 through cannula 68 until electrodes 114 of the lead are placed correctly within patient 12 (148). As previously described, test electrical stimulation signals may be delivered to patient 12 via electrodes 114 of lead 108 in order to confirm placement of lead 108. In other examples, other medical devices such as stimulation module 116 may be implanted via cannula 68. The user then removes cannula 68 from lead 108 (150). Removal of cannula 68 from lead 108 may cause fixation devices attached to the lead to deploy into surrounding tissue, such as the extension of tines 112 that anchor the lead within patient 12. In some embodiments, the user may finish implantation of system 10 by tunneling the proximal end of lead 108 through patient 12 to an implant site for stimulator 14 and couple the lead to stimulator 14 (152). In some embodiments, additional tunneling may be performed by implant tool 50 and/or cannula 68.

Figure 15A:
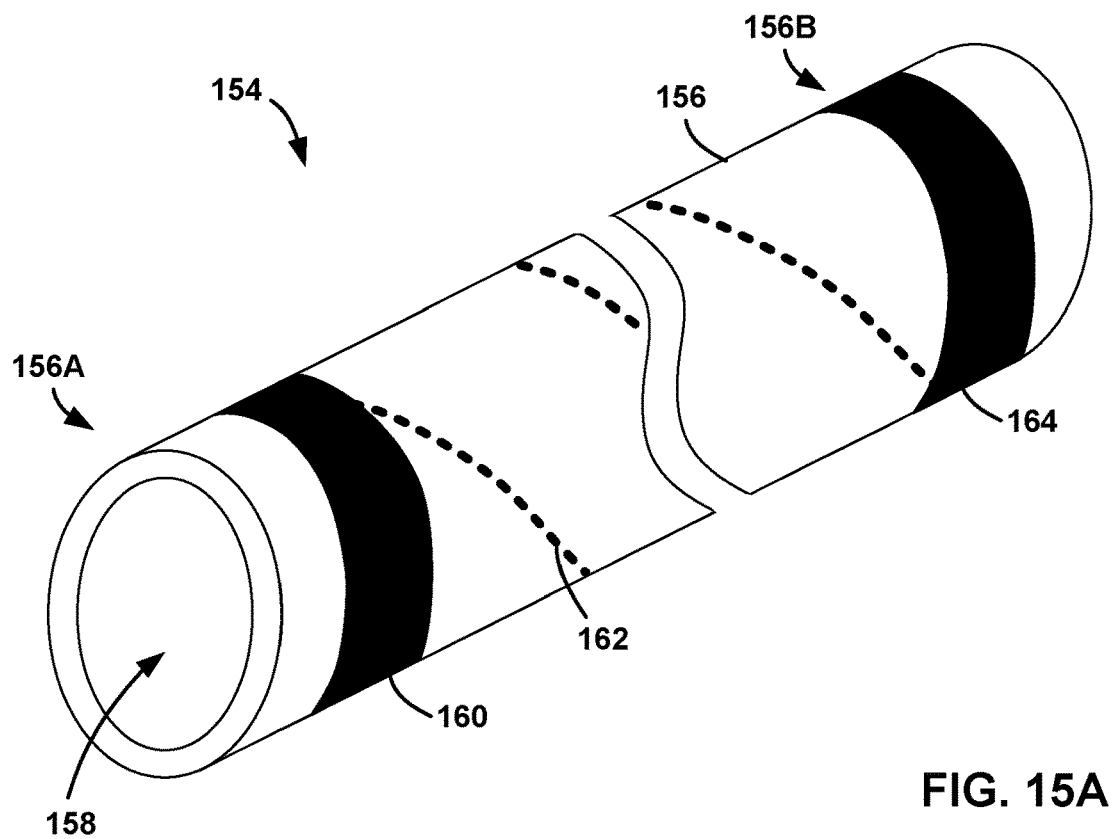
FIGS. 15A and 15B are conceptual diagrams of example cannulas having an electrode to provide test stimulation to a patient.
Figure 15B:
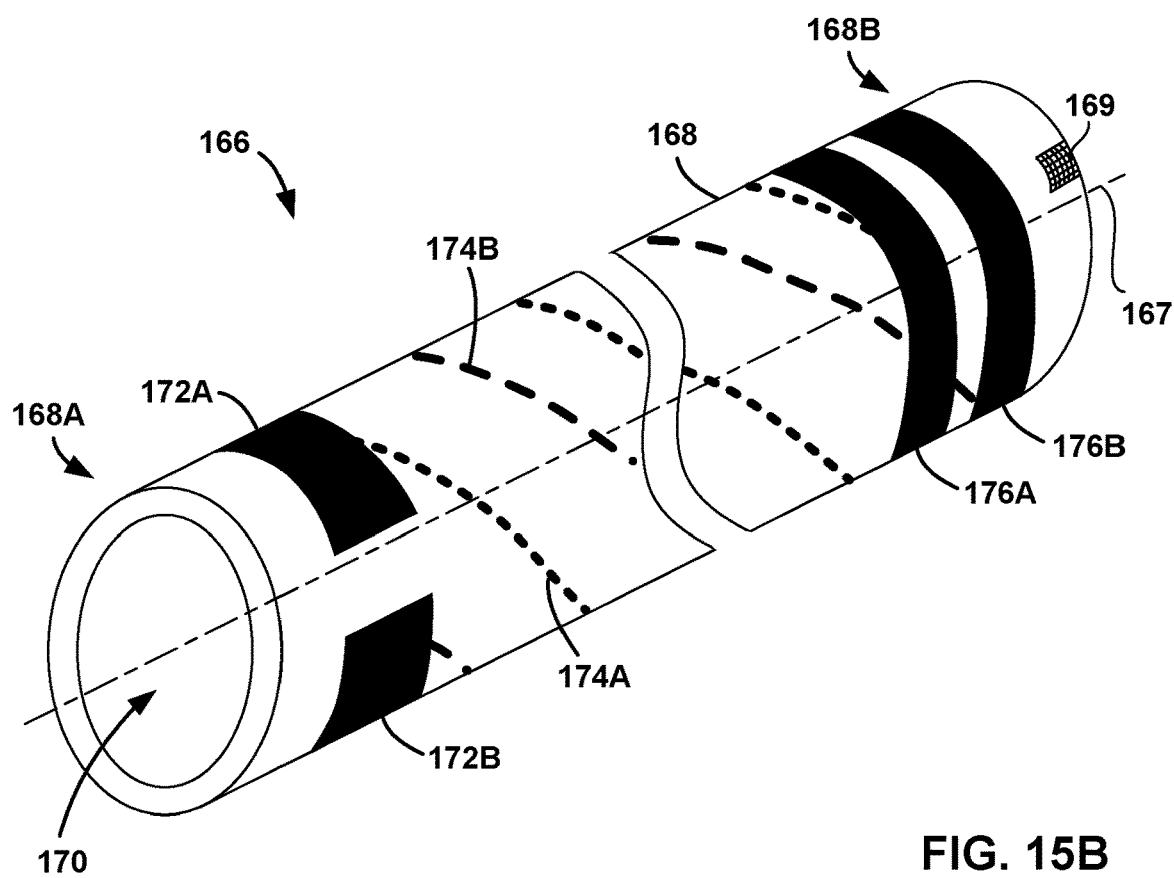

FIGS. 15A and 15B are conceptual diagrams of example cannulas 154 and 166 including one or more electrodes to provide test stimulation to a patient in order to determine a placement of the cannula 154, 156 relative to a target tissue site or in order to determine a location of the target tissue site relative to the cannula 154, 156. Cannulas 154 and 166 may be similar to cannulas 68 (FIGS. 4A-4B) and 104 (FIGS. 8A-8B). However, cannulas 154 and 166 may aid the user in locating the target site for stimulation or other therapy delivery. As shown in FIG. 15A, cannula 154 includes elongated housing 156 that defines lumen 158.

Cannula 154 also includes electrode 160 located at distal portion 156A and electrical contact 164 located at proximal portion 156B. Electrical contact 164 and electrode 160 are electrically coupled via conductive element 162 (shown in phantom lines). Test stimulation may be delivered to patient 12 via electrode 160 of cannula 154 in order to aid the user in locating the target site for stimulation therapy or determine a relative location between distal portion 156A of cannula 154 and the target therapy delivery site. Electrode 160 may simulate an electrode of a medical device implanted through cannula 154 without requiring the user to remove the needle of an implant tool.

In addition, stimulation delivered by electrode 160 may be useful for adjusting a position of implant tool 178 (FIGS. 16A-16B) within the patient by providing a mechanism for determining a location of the target site relative to electrode 160 of cannula 154. For example, upon delivering test stimulation via electrode 160 and receiving patient feedback or observing any other patient reactions to the stimulation, the user may determine that electrode 160 is positioned a significant distance from the target tissue site. Thus, based on information generated by delivering test stimulation via electrode 160, the user may adjust the position of implant tool 178, such as by at least partially withdrawing implant tool 178 and cannula 154 from the patient and reinserting the implant tool and cannula into the patient in a direction that may be closer to the target tissue site.

Figure 16A:
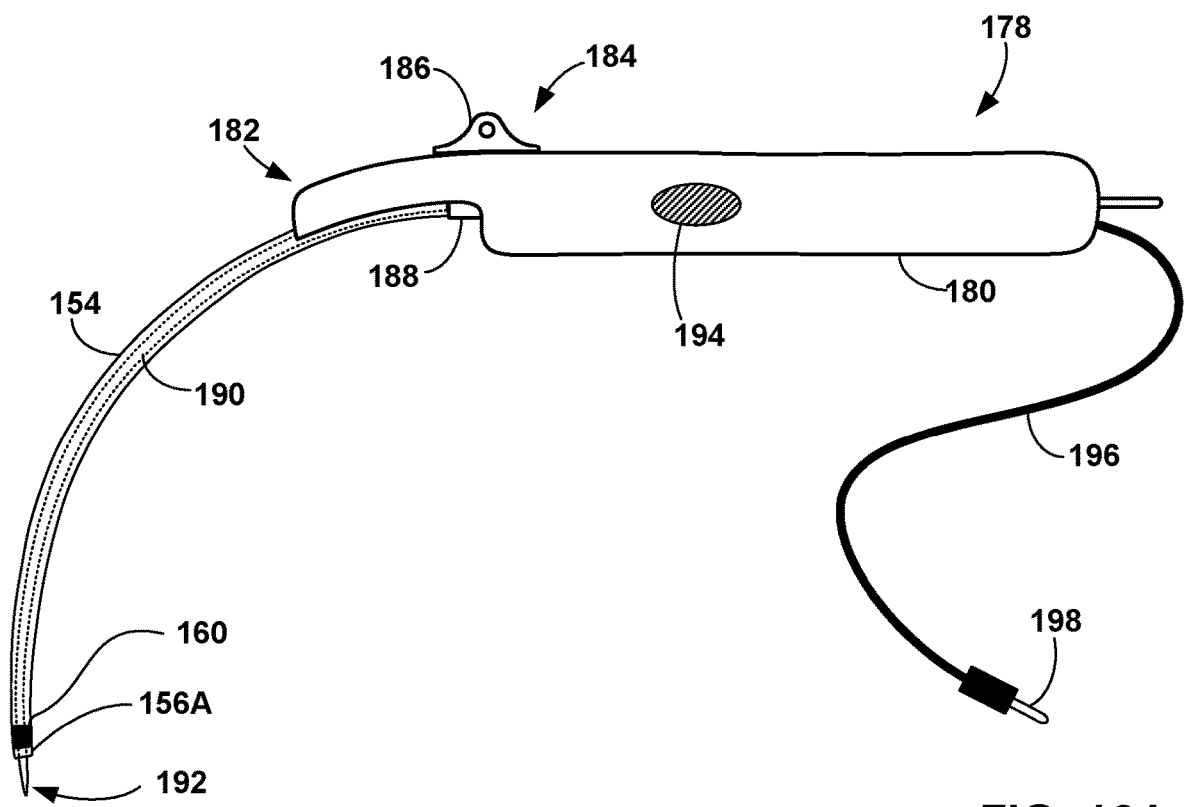
FIG. 16A is a side view of an example implant tool that provides test stimulation to a patient.
Figure 16B:
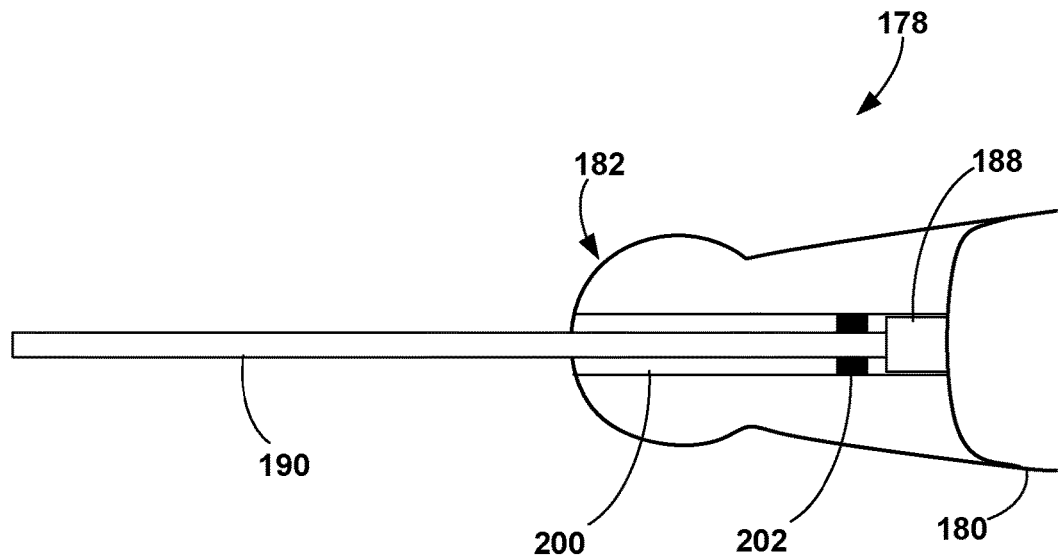
FIG. 16B is a bottom view of an example implant tool having an electrical contact to electrically connect to a cannula that delivers test stimulation.

Electrical contact 164 is provided on the outsider surface of cannula 154 to couple to a corresponding contact of implant tool 178 (FIGS. 16A and 16B). The coupling between the electrical contacts of cannula 154 and implant tool 178 enables a stimulation signal to be transferred between a stimulation signal source and electrode 160. The stimulation signal is transmitted from electrical contact 164, through conductive element 162, and to electrode 160 where the signal reaches tissue of patient 12. In other examples, electrical contact 164 may be located in lumen 158 of elongated housing 156 to couple to a contact located on the needle of the implant tool.

In the embodiment shown in FIG. 15A, conductive element 162 is generally located within the material of elongated housing 156 to insulate both the needle and surrounding tissue from the electrical signal conducted through the conductive element. In other embodiments, conductive element 162 may be electrically insulated and disposed along an outer surface of cannula 154 or along an inner lumen 158 of cannula 154, rather than substantially embedded within housing 156. Conductive element 162 may be provided in a helical or spiral arrangement within elongated housing 156. The helical shape of conductive element 162 may allow the conductive element to bend with elongated housing 156 while reducing mechanical stress to the conductive element. In other embodiments, conductive element 162 may be positioned generally straight along a side of elongated housing 156 if cannula 154 bending may be minimal during the implantation procedure. In addition, cannula 154 may have multiple ring, partial ring or segmented electrodes located along the length of elongated housing 156 in addition to electrode 160, similar to lead 108. Each electrode may be coupled to separate electrical contacts via separate conductive elements so that a separate signal may be delivered to each of the multiple electrodes.

Two or more electrodes on cannula 154 may be useful for, for example, providing electrodes for bipolar stimulation. If cannula 154 includes a single electrode 160, the test electrical stimulation may be delivered between electrode 160 and an external ground pad attached to an external surface of patient 12 or between electrode 160 and conductive needle 62 (or vice versa, the stimulation may be delivered from needle 62 to electrode 160, which acts as a ground). On the other hand, if cannula 154 includes multiple electrodes, stimulation may be delivered between at least two of the electrodes.

As shown in FIG. 15B, another embodiment of cannula 166 includes elongated housing 168 that defines lumen 170. Cannula 166 also includes electrodes 172A and 172B (collectively "electrodes 172) located at distal portion 168A and electrical contacts 176A and 176B (collectively "electrical contacts 176") located at proximal portion 168B. Electrical contacts 176 and electrodes 172 are electrically coupled via separate conductive elements 174A and 174B (collectively "conductive elements 174").

Cannula 166 delivers test stimulation to patient 12 via at least one of electrodes 172 in order to aid the user in locating the target site for stimulation therapy or determining a relative position between cannula 166 and the target site. Electrodes 172 may simulate an electrode of a medical device implanted through cannula 166 without requiring the user to remove the needle of an implant tool before testing the position of the cannula. Each of electrodes 172 are semi-circular in cross-section (e.g., partial ring or segmented electrodes) located on a circumferential subsection of the substantially cylindrical housing 168. For example, electrodes 172 may each extend around less than one-half of the outer circumference of elongated housing 168. In the embodiment shown in FIG. 15B, electrodes 172A and 172B have different circumferential positions on cannula 166.

Discrete use of one of electrodes 172 may allow the user to locate the exact location of the target site. For example, the user may deliver stimulation via one of electrodes 172 in order to determine which side of cannula 166 the target tissue site is located. Once the user knows which side of cannula 166 is adjacent to the target site, the user may be able to implant a medical device configured to direct stimulation to that particular site or redirect implant tool 178 (FIGS. 16A-B) toward the target site. An example medical device may be a lead with segmented electrodes or a complex electrode array located around the perimeter of the lead. This type of medical device may need to be correctly oriented in the circumferential position before insertion into cannula 166 to retain the direction information obtained from the test stimulation.

Cannula 166 may include marker 169 with which segmented or partial ring electrodes may be aligned in order to ensure that the segmented or partial ring electrodes are implanted in a desired orientation. For example, marker 169 may be aligned with one of electrodes 172A, 172B in order to indicate the direction in which the electrode 172A or 172B faces. In other embodiments, cannula 166 may include more than one marker (e.g., one marker per electrode). Marker 169 may be a printed marker on cannula 166, an indentation in cannula 166, a radiographic marker, or another type of marker that is visible or otherwise detectable (e.g., detectable by a radiographic device) by a user. In addition, in some embodiments, marker 169 may be placed at proximal portion 168B of cannula 166 such that marker 169 remains visible to the user when cannula 166 is partially implanted within patient 12. In other embodiments, other types of indicator techniques may be used to identify a relative location of one or more segmented or partial ring electrodes, such as luer lock wings on cannula 166.

While effective stimulation may still be provided to patient 12 despite the segmented electrodes of a lead not facing toward the target tissue site, implanting the lead such that the segmented electrodes face toward the target stimulation site may help reduce the amount of power consumed by an electrical stimulator. That is, delivering stimulation via segmented electrodes that face toward the target stimulation site may be a more efficient use of stimulation energy because substantially the same results may achieved with less energy as compared to delivering stimulation via segmented electrodes facing away from the target stimulation site.

In other examples of cannula 166, the cannula may have only one semi-circular electrode or more than two electrodes around the perimeter of the elongated housing. In addition, some examples of cannula 166 may include multiple groups of electrodes 172 along the length of distal portion 168A.

Electrical contacts 176 are provided on the outside of elongated housing 168 to couple to corresponding contacts of an implant tool similar to implant tool 178 (FIGS. 16A and 16B) to transfer the stimulation signal. The stimulation signal is transmitted from electrical contacts 176, through conductive elements 174, and to electrodes 172 where the signal reaches tissue of patient 12. In other examples, electrical contact 176 may be located in lumen 170 of elongated housing 168 to couple to contacts located on the needle of the implant tool. Alternative examples of cannula 166 may include electrical contacts 176 embodied as semi-circular elements positioned around the perimeter of proximal portion 168B, similar to the placement of electrodes 172.

Conductive elements 174 are generally located within the material of elongated housing 168 to insulate both the needle and surrounding tissue from the electrical signal conducted through the conductive elements. In other embodiments, conductive elements 172 may be electrically insulated and disposed along an outer surface of cannula 166 or along an inner lumen 170 of cannula 166, rather than substantially embedded within housing 168. Conductive elements 174 may be provided in a helical or spiral arrangement within elongated housing 168. The helical shape of conductive element 174 may allow the conductive elements to bend with elongated housing 168 while reducing mechanical stress to the conductive elements. In other embodiments, conductive elements 174 may be positioned generally straight along a side of elongated housing 168 if cannula 166 bending may be minimal during the implantation procedure.

In other embodiments, a cannula may include a single stimulation electrode 172A or 172B that extends around less than one hundred percent of the outer perimeter of housing 168 of cannula 166. The user may deliver stimulation to determine a direction of the target tissue site relative to electrode 172A or 172B and rotate cannula 166 within the patient (i.e., rotate cannula 166 along longitudinal axis 167) as needed in order to "search" in different directions for the target tissue site with the test stimulation. Cannula 166 is typically relatively rigid, thus, minimizing the possibility of torsion (i.e., twisting) of cannula 166 when the user rotates cannula 166 while cannula 166 is disposed within patient 12s.

Cannulas 154 and 166 may be constructed of a biocompatible material that is flexible to bend according to the shape of needle 190 (FIGS. 16A and 16B), similar to cannulas 68 or 104. Suitable materials may include polymers such as polyurethane, polyethylene, vinyl, expanded-polytetrafluoroethylene (ePTFE), or other polymers. Alternatively, cannula 68 may be constructed of a material that has a shape memory so that the cannula forms to a predetermined shape once removed from the needle. Examples of suitable shape memory materials include, but are not limited to, a copper-zinc-aluminium alloy, copper-aluminium-nickel alloy, a nickel-titanium alloy (e.g., Nitinol) or ethylene tetrafluoroethylene (ETFE). Cannula 68 may be constructed of other plastics capable of being thermoset, or heated to a certain shape. Nitinol may provide an additional benefit in that it may be more readily visualized during fluoroscopy.

FIG. 16A is a side view of an example implant tool 178 that provides test stimulation to patient 12. Implant tool 178 is substantially similar to implant tool 50. Cannula 154 is described in combination with implant tool 187, but cannula 166 may also be used in some examples. As shown in FIG. 16A, implant tool 178 includes housing 180, flange 182, release mechanism 184, grip 186, guide 188, needle 190, and cable 196. As shown in FIG. 16A, cannula 154 is fitted over needle 190 and substantially conforms to the shape of the needle. The length of cannula 154 is slightly shorter than the exposed length of needle 190 to allow piercing tip 192 of the needle to extend past the end of the cannula. A user may hold implant tool 178 via housing 180 while guiding introducing needle 190 and cannula 154 through tissue of a patient via piercing tip 192.

Cannula 154 is fitted over at least a portion of needle 190 and proximal portion 156B of the cannula resides against guide 188 of release mechanism 184. In the embodiment shown in FIG. 16A, cannula 154 also rests against flange 182 of housing 180 and against needle 190. However, as described above, in other embodiments, cannula 154 does not necessarily contact flange 182 until a sufficient force is applied to needle 190 and cannula 154. Flange 182 transmits force from housing 180 to cannula 154 and needle 190 to allow the user to push piercing tip 192 through tissue of patient 12 and minimize unwanted flexing of the needle. In some examples, flange 182 may resides around a greater surface area of cannula 154 to support forces in multiple directions from the user.

The user may deliver test stimulation to patient 12 via cannula 154 in order to verify the placement of distal portion 156A of the cannula relative to a target tissue site as well as to locate a target tissue site. In some embodiments, implant tool 178 may include a signal generator similar to stimulator 14A that generates a stimulation signal. Implant tool 178 may receive power via cable 196 and plug 198 when the plug is coupled to an electrical outlet. The signal generator of implant tool 178 may have predefined parameters set for test stimulation. The user may press button 194 to deliver the test stimulation via cannula 154. Alternatively, implant tool 178 include any of a processor, memory, user interface, or telemetry circuit to program the desired test stimulation parameters into the implant tool. In other examples, implant tool 178 may be coupled to an external signal generator via cable 196 and plug 198 that generates the stimulation signal for test stimulation.

The user may continue to reposition needle 190 and cannula 154 and deliver additional test stimulations to patient 12 via electrode 160 until the user verifies correct placement of distal portion 156A adjacent to the target site. Once distal portion 156A of cannula 154 is positioned adjacent to the target site, the user may utilize release mechanism 184 to initiate movement between cannula 154 and needle 190. In the embodiment shown in FIG. 16A, the user may pushes against grip 186 of release mechanism 184 while withdrawing the needle from the cannula with housing 180. A medical device may then be implanted within the patient via lumen 158 of cannula 154.

FIG. 16B shows the bottom side of implant tool 178 without a cannula placed over needle 190. Flange 182 defines channel 200 between the flange and needle 190. A cannula, such as cannula 154, may slide between within channel 200. Guide 188 of release mechanism 184 engages with the proximal portion of the cannula to facilitate the removal of the cannula from needle 190. In some examples, the cannula may extend to a position within housing 180 if a longer cannula is needed for implantation of the medical device.

Implant tool 178 also includes electrical contact 202 disposed within channel 200 of flange 182. Electrical contact 202 is positioned to contact electrical contact 164 of cannula 154, for example, and transmit the test stimulation signal to the cannula. In other examples, electrical contact 202 may be disposed on needle 190, in which case electrical contact 164 of cannula 154 may be located within lumen 158. Alternatively, implant tool 178 may have multiple electrical contacts within channel 200 in order to deliver test stimulation to a cannula with any number of electrical contacts. In this manner, implant tool 178 may be used with any of cannulas 154, 166 or other cannulas that include at least one electrode.

Test stimulation may only be delivered to electrical contacts of implant tool 178 that are coupled to a cannula electrical contact that completes a circuit. Thus, if implant tool 178 is withdrawn from cannula 154, the contact between electrical contact 202 and electrical contact 164 of cannula 154 may be interrupted, and test stimulation may not be delivered to patient 12 via electrode 160.

Figure 17:
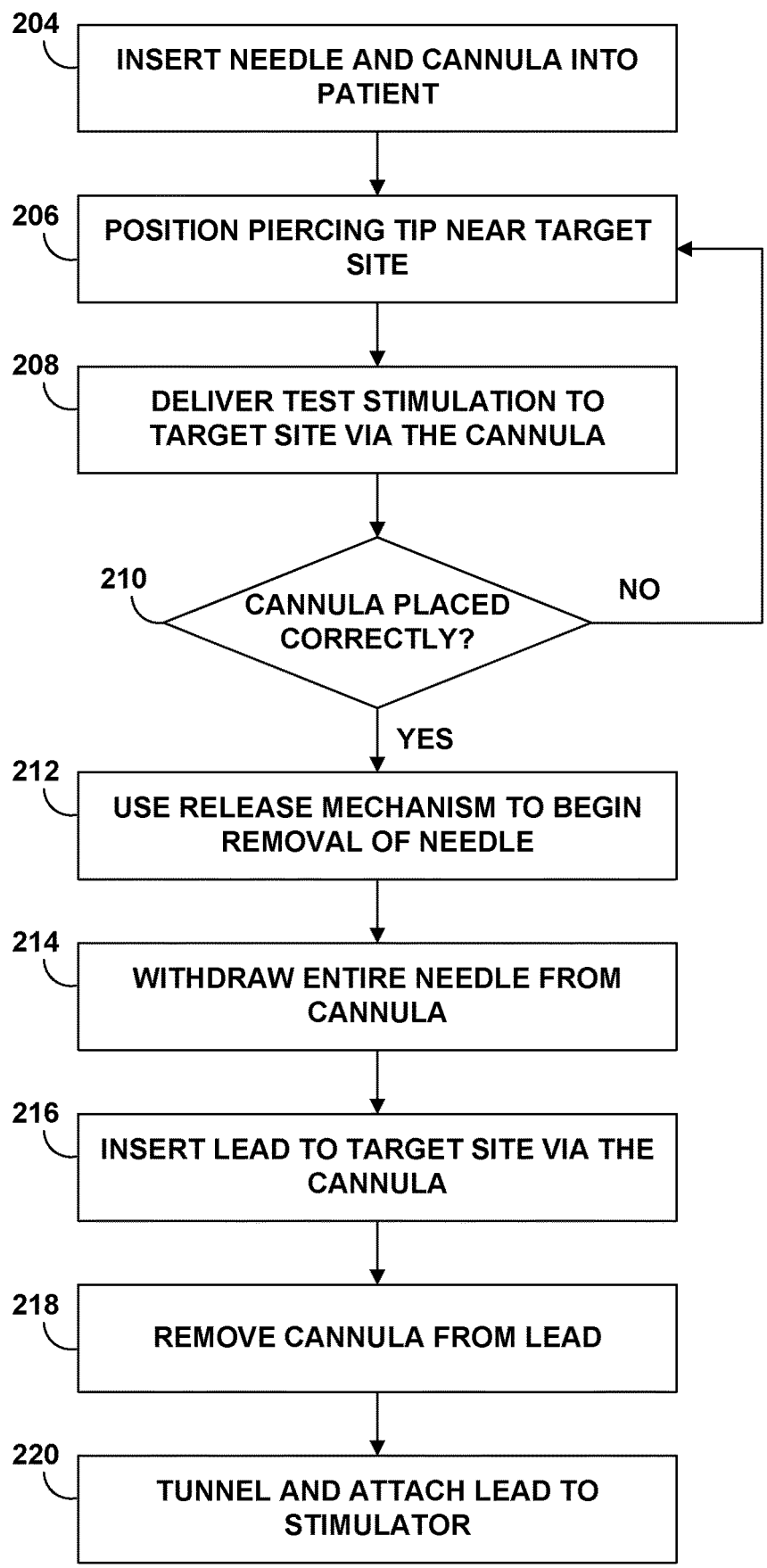
FIG. 17 is a flow diagram of an example technique for implanting a medical device within a patient with the aid of a cannula including one or more electrodes for providing test stimulation to a patient.

FIG. 17 is a flow diagram of an example technique for implanting a medical device within a patient with the aid of a cannula including one or more electrodes for providing test stimulation to a patient. Implant tool 178 and cannula 154 will be used in the example of FIG. 17, although a similar technique may be used with cannula 166 (FIG. 15B). As shown in FIG. 17, the user begins implantation by inserting cannula 154 into patient 12 through the use of needle 190 of implant tool 178 (204). Piercing tip 192 of needle 190 may define an insertion path through tissue of the patient. The user continues inserting, or tunneling, needle 190 into patient 12 until piercing tip 192 of the needle is positioned near the target site (206).

The user delivers test stimulation with implant tool 178 to the target site via electrode 160 of cannula 154 (208). If the user verifies that cannula 154 is not positioned correctly based on the feedback of patient 12 or other physiological responses of patient 12 to the test stimulation (210), the user repositions piercing tip 192 of needle 190 near the estimated target site (206). As previously described, if electrode 160 of cannula 154 is a partial ring or segmented electrode, the test stimulation delivered via electrode 160 may also be used to determine the approximate location of the target site and readjust the position of needle 190 and cannula 154 within patient. If the user verifies that cannula 154 is correctly positioned adjacent to the target site (210), the user uses release mechanism 184 to begin the removal of the cannula while simultaneously withdrawing needle 190 from the cannula (212).

The user continues to withdraw needle 190 from cannula 154 until the entire needle exits the cannula (214). With cannula in place within the insertion path previously defined by the piercing tip 192 of needle 190, the user may advance lead 108 through cannula 154 until electrodes 114 of the lead are placed correctly within patient 12, i.e., correctly positioned relative to the target site (216). In other examples, other medical devices, such as stimulation module 116 or a fluid delivery catheter, may be implanted via cannula 154. After lead 108 is correctly positioned relative to the target tissue site, the user may remove cannula 154 from lead 108 (218). The relative position between lead 108 and the target tissue site may be confirmed via test stimulation delivered via one or more electrodes 114 of lead 108. Fixation devices attached to the lead may deploy into tissue as cannula 154 is removed from patient 12. In some embodiments, the user may tunnel the proximal portion of lead 108 through patient 12 in order to couple the lead to stimulator 14 (220). In other examples, additional tunneling may be performed by implant tool 178 and/or cannula 154.

Figure 18:
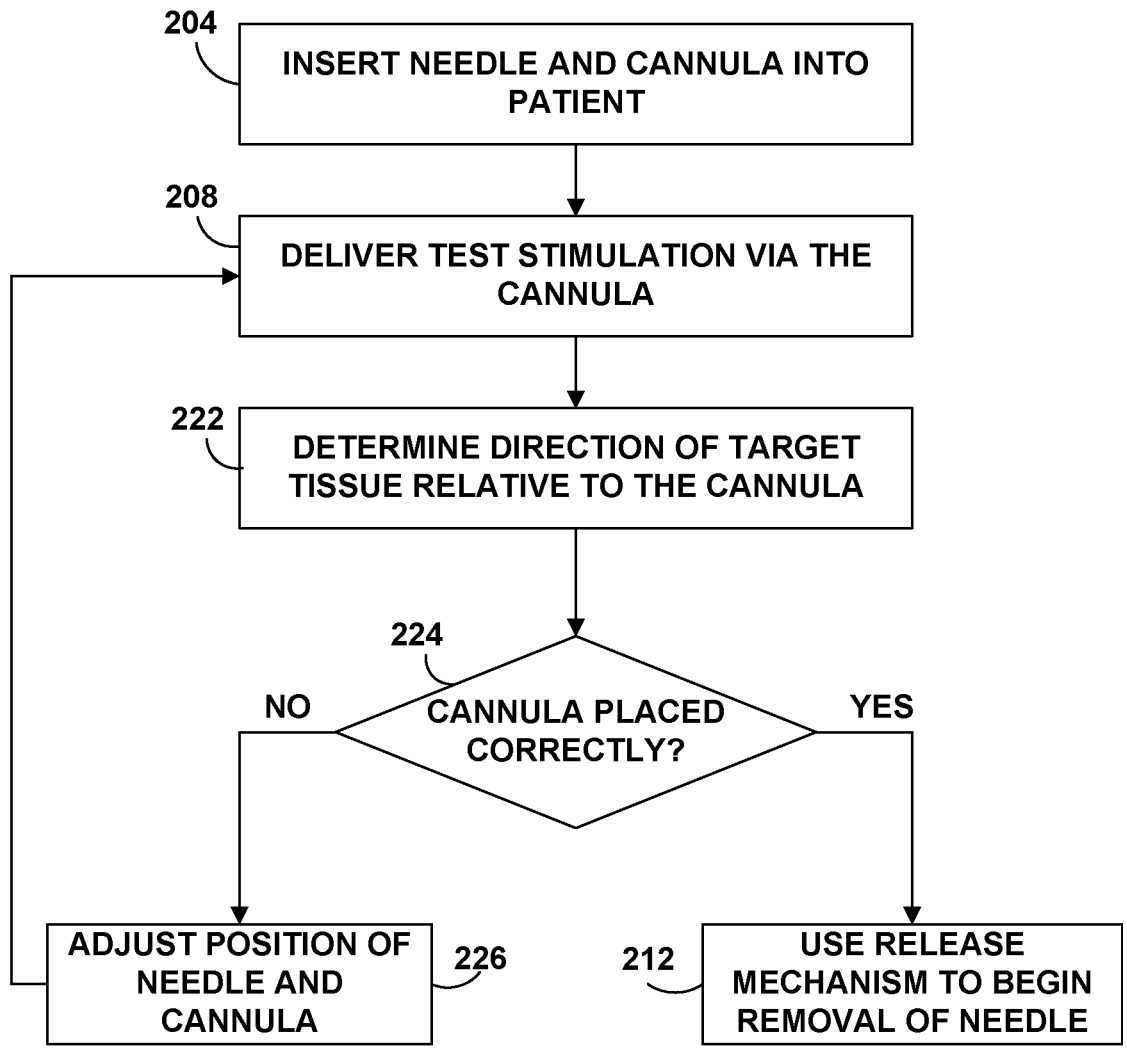
FIG. 18 is a flow diagram of an example technique for locating a target tissue site within a patient with the aid of a cannula including one or more electrodes for providing test stimulation to a patient.

FIG. 18 is a flow diagram of an example technique for locating a target tissue site within a patient with the aid of a cannula including one or more electrodes for providing test stimulation to a patient. As in the technique shown in FIG. 17, a needle and cannula are inserted into patient 12 (204) and test stimulation is delivered to patient 12 via at least one of electrodes 172 of cannula 166 (206). In other embodiments, cannula 154 may be used in the technique shown in FIG. 18 if electrode 160 comprises a partial ring or segmented electrode. Based on patient feedback to the test electrical stimulation or other physiological responses (e.g., a muscle contraction) to the electrical stimulation, the user may determine a location of the target tissue relative to the direction in which stimulation was directed (222). For example, if stimulation is delivered via electrodes 172 of cannula 166 at different times, patient feedback to the stimulation via electrode 172A may be compared to the patient feedback to the stimulation via electrode 172B. The comparison may indicate whether the target tissue site is closer to stimulation electrode 172A or 172B. Any number of stimulation electrodes may be used. If a single partial ring or segmented electrode is used to deliver the test stimulation to patient 12, the user may rotate cannula 166 about longitudinal axis 167 and compare the patient response to the different rotational positions of cannula 166 in order to determine the approximate location of the target tissue relative to the cannula (222).

If the test stimulation indicates that cannula 166 is placed correctly relative to the target site (224), the user may user the release mechanism 184 of implant tool 178 to initiate withdrawal of needle 190 from cannula 166 (212). On the other hand, if the test stimulation indicates that cannula 166 is not placed correctly relative to the target site (224), the user may adjust the position of needle 190 and cannula 166 within the patient, such as by withdrawing the needle 190 partially or completely from patient 12 and reinserting needle 190 into patient 12 toward the approximate location of the target site (226). Test electrical stimulation may then be delivered via cannula 166 (208), and so forth until the user determines that cannula 166 is correctly placed relative to the target site (224).

Many embodiments of the invention have been described. Various modifications may be made without departing from the scope of the claims. These and other embodiments are within the scope of the following claims.

The invention claimed is:

1. A medical device comprising:
an implant tool configured to define an insertion path through tissue of a patient, wherein the implant tool comprises:
an elongated body defining a lumen, wherein the elongated body comprises a proximal section and a distal section, the distal section defining a portion of the lumen and comprising a conductive portion that extends around less than an entire outer perimeter of the elongated body; and
an electrical contact positioned at the proximal section of the elongated body and electrically connected to the conductive portion;
wherein the implant tool further comprises a needle configured to fit within the lumen defined by the elongated body, wherein the elongated body is shorter than the needle to enable a distal tip of the needle to extend past a distal end of the elongated body when the needle is received within the lumen defined by the elongated body.

2. The medical device of claim 1, wherein the conductive portion comprises a partial ring electrode or a segmented electrode.

3. The medical device of claim 1, further comprising a conductive element within the elongated body and electrically coupling the conductive portion to the electrical contact.

4. The medical device of claim 1, wherein the conductive portion comprises a first conductive portion, and wherein the elongated body comprises a plurality of conductive portions comprising the first conductive portion, the conductive portions of the plurality of conductive portions being located at different circumferential positions around the elongated body.

5. The medical device of claim 4, wherein the electrical contact comprises a first electrical contact, and wherein the elongated body comprises a plurality of electrical contacts positioned at the proximal section of the elongated body, the plurality of electrical contacts comprising the first electrical contact, wherein each electrical contact of the plurality of electrical contacts is electrically coupled to a respective conductive portion of the plurality of conductive portions via respective conductive elements.

6. The medical device of claim 1, wherein the needle is malleable.

7. The medical device of claim 1, wherein the elongated body comprises a shape memory material.

8. The medical device of claim 1, wherein the elongated body is constructed from a metal.

9. The medical device of claim 1, wherein the elongated body is constructed from a polymer.

10. The medical device of claim 1, wherein the elongated body further comprises a marker aligned with the conductive portion to indicate a direction in which the conductive portion faces.

11. An assembly comprising:
the medical device of claim 1; and
an implantable medical lead comprising a plurality of electrodes, wherein the implantable medical lead is configured to be received in the lumen defined by the elongated body.

12. An assembly comprising:
the medical device of claim 1; and
an implantable medical device comprising electrical stimulation generation circuitry, wherein the implantable medical device is configured to be received in the lumen defined by the elongated body.

13. A system comprising:
an implant tool configured to define an insertion path through tissue of a patient, wherein the implant tool comprises:
an elongated body defining a lumen, wherein the elongated body comprises a proximal section and a distal section, the distal section defining a portion of the lumen and comprising a conductive portion that extends around less than an entire outer perimeter of the elongated body; and
an electrical contact positioned at the proximal section of the elongated body and electrically connected to the conductive portion;
wherein the implant tool further comprises a needle configured to fit within the lumen defined by the elongated body, wherein the elongated body is shorter than the needle to enable a distal tip of the needle to extend past a distal end of the elongated body when the needle is received within the lumen defined by the elongated body; and
stimulation circuitry configured to generate electrical stimulation, wherein the conductive portion of the elongated body is configured to be electrically connected to the stimulation circuitry via the electrical contact to deliver the electrical stimulation to tissue of a patient.

14. The system of claim 13, further comprising a processor configured to control the stimulation circuitry to generate the electrical stimulation based on a predefined set of electrical stimulation parameter values.

15. The system of claim 13, further comprising:
a user interface; and
a processor configured to control the stimulation circuitry to generate the electrical stimulation based on electrical stimulation parameter values received from a user via the user interface.

16. The system of claim 13, wherein the conductive portion comprises a first conductive portion, and wherein the elongated body comprises a plurality of conductive portions comprising the first conductive portion, the conductive portions of the plurality of conductive portions being located at different circumferential positions around the elongated body.

17. A method comprising:
advancing an implant tool through tissue of a patient to a target site within the patient to position a conductive portion of the implant tool proximate a sacral nerve of the patient, wherein the implant tool is configured to define an insertion path through the tissue and comprises:
an elongated body defining a lumen, wherein the elongated body comprises a proximal section and a distal section, the distal section defining a portion of the lumen and comprising the conductive portion that extends around less than an entire outer perimeter of the elongated body; and
an electrical contact positioned at the proximal section of the elongated body and electrically connected to the conductive portion; and
delivering electrical stimulation to the patient via the conductive portion of the elongated body.

18. The method of claim 17, wherein advancing the implant tool to the target site comprises advancing the distal section of the elongated body through a foramen in a sacrum of the patient.

19. The method of claim 17, wherein delivering the electrical stimulation to the patient comprises delivering a first test stimulation to the patient via the conductive portion, the method further comprising rotating the elongated body and delivering a second test stimulation to the patient via the conductive portion.

20. The method of claim 17, further comprising adjusting a position of the elongated body within the patient after delivering the electrical stimulation to the patient.

21. The method of claim 20, wherein adjusting the position of the elongated body comprises adjusting a depth of the elongated body within the patient.

22. The method of claim 17, wherein delivering the electrical stimulation to the patient comprises delivering a first test stimulation to the patient in a first direction, the method further comprising, after delivering the first test stimulation:
rotating the elongated body within the patient about a longitudinal axis of the elongated body; and
delivering a second test stimulation to the patient via the conductive portion in a second direction different from the first direction.

23. The method of claim 17, wherein the conductive portion comprises a first conductive portion, and wherein the elongated body comprises a plurality of conductive portions including the first conductive portion and a second conductive portion, the conductive portions of the plurality of conductive portions being located at different circumferential positions around the elongated body, and wherein delivering the electrical stimulation to the patient comprises delivering a first test stimulation to the patient via the first conductive portion, the method further comprising, after delivering the first test stimulation, delivering a second test stimulation to the patient via the second conductive portion.

24. The method of claim 17, further comprising introducing a medical device into the lumen of the elongated body.

25. The method of claim 24, wherein the medical device comprises an implantable medical lead or an implantable medical device comprising electrical stimulation generation circuitry.

26. The method of claim 17, wherein the implant tool further comprises a needle configured to fit within the lumen defined by the elongated body, wherein the elongated body is shorter than the needle to enable a distal tip of the needle to extend past a distal end of the elongated body when the needle is received within the lumen defined by the elongated body.

27. The method of claim 26, further comprising removing the needle from the lumen of the elongated body, wherein after removing the needle from the lumen, the elongated body changes from a first shape to a second shape.

\* \* \* \* \*